US012403322B2

(12) United States Patent
Ballard et al.

(10) Patent No.: US 12,403,322 B2
(45) Date of Patent: Sep. 2, 2025

(54) MODULAR INGRESS PROTECTED ELECTRODE SYSTEM FOR A WEARABLE DEFIBRILLATOR

(71) Applicant: ZOLL MEDICAL CORPORATION, Chelmsford, MA (US)

(72) Inventors: Dale Ballard, Glenshaw, PA (US); Robert J. Hulings, Mars, PA (US); Scott D. Quinnell, Kittanning, PA (US); Ronald A. Seman, Pittsburgh, PA (US); Richard S. Sharbaugh, New Kensington, PA (US); Brian D. Snyder, Pittsburgh, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 571 days.

(21) Appl. No.: 17/592,886

(22) Filed: Feb. 4, 2022

(65) Prior Publication Data

US 2022/0249854 A1    Aug. 11, 2022

Related U.S. Application Data

(60) Provisional application No. 63/146,763, filed on Feb. 8, 2021.

(51) Int. Cl.
*A61N 1/39* (2006.01)
*A61N 1/04* (2006.01)

(52) U.S. Cl.
CPC ....... *A61N 1/39046* (2017.08); *A61N 1/0484* (2013.01); *A61N 1/3931* (2013.01); *A61N 1/3968* (2013.01)

(58) Field of Classification Search
CPC .............. A61N 1/39046; A61N 1/0484; A61N 1/3931; A61N 1/3968; A61N 1/046
See application file for complete search history.

(56) References Cited

U.S. PATENT DOCUMENTS

| 4,094,310 A | 6/1978 | McEachern et al. |
| 4,632,122 A | 12/1986 | Johansson et al. |

(Continued)

FOREIGN PATENT DOCUMENTS

| DE | 2644236 C3 | 4/1981 |
| EP | 0 459 239 A2 | 12/1991 |

(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.

(Continued)

*Primary Examiner* — James M Kish
*Assistant Examiner* — James Moss
(74) *Attorney, Agent, or Firm* — Lando & Anastasi, LLP

(57) ABSTRACT

A modular waterproof therapeutic electrode component for preventing water ingress and for easy servicing. The component comprises a substrate comprising a conductive surface, a reservoir of conductive fluid mounted on the substrate, a reusable waterproof enclosure comprising circuitry, the reusable waterproof enclosure comprising circuitry configured to be removably coupled to the substrate, and a fluid deployment device in electrical communication with the circuitry and mounted on the substrate, the fluid deployment device configured to cause the reservoir to release the conductive fluid onto the conductive surface to reduce electrical impedance between the conductive surface and skin of a subject.

21 Claims, 18 Drawing Sheets

(56) References Cited

U.S. PATENT DOCUMENTS

| | | |
|---|---|---|
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,348,008 A | 9/1994 | Bornn et al. |
| 5,357,696 A | 10/1994 | Gray et al. |
| 5,365,932 A | 11/1994 | Greenhut |
| 5,472,453 A | 12/1995 | Alt |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,532,379 B2 | 3/2003 | Stratbucker |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,908,437 B2 | 6/2005 | Bardy |
| 6,944,498 B2 | 9/2005 | Owen et al. |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,522,951 B2 | 4/2009 | Gough et al. |
| 7,831,303 B2 | 11/2010 | Rueter et al. |
| 7,974,689 B2 | 7/2011 | Volpe et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 9,008,801 B2 | 4/2015 | Kaib et al. |
| 9,427,564 B2 | 8/2016 | Kaib et al. |
| 9,457,178 B2 | 10/2016 | Kaib et al. |
| 9,956,392 B2 | 5/2018 | Kaib et al. |
| 10,183,160 B2 | 1/2019 | Kaib et al. |
| 11,571,561 B2 | 2/2023 | Quinnell et al. |
| 2003/0004547 A1 | 1/2003 | Owen et al. |
| 2003/0055460 A1 | 3/2003 | Owen et al. |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0007970 A1 | 1/2004 | Ma et al. |
| 2004/0162510 A1 | 8/2004 | Jayne et al. |
| 2004/0249419 A1 | 12/2004 | Chapman et al. |
| 2005/0049515 A1 | 3/2005 | Misczynski et al. |
| 2005/0131465 A1 | 6/2005 | Freeman et al. |
| 2006/0036292 A1 | 2/2006 | Smith et al. |
| 2006/0085049 A1 | 4/2006 | Cory et al. |
| 2006/0211934 A1 | 9/2006 | Hassonjee et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0028821 A1 | 2/2007 | Bennett et al. |
| 2007/0060993 A1 | 3/2007 | Craige et al. |
| 2007/0073120 A1 | 3/2007 | Li et al. |
| 2007/0118056 A1 | 5/2007 | Wang et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0249591 A1 | 10/2008 | Gaw et al. |
| 2008/0306560 A1 | 12/2008 | Macho et al. |
| 2008/0306562 A1 | 12/2008 | Donnelly et al. |
| 2008/0306566 A1 | 12/2008 | Holmstrom et al. |
| 2008/0312709 A1 | 12/2008 | Volpe et al. |
| 2009/0073991 A1 | 3/2009 | Andrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Ibbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0088652 A1 | 4/2009 | Tremblay |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0234716 A1 | 9/2010 | Engel |
| 2010/0298899 A1 | 11/2010 | Donnelly et al. |
| 2011/0077728 A1 | 3/2011 | Li et al. |
| 2011/0245711 A1* | 10/2011 | Katra ............... A61B 5/0075 600/547 |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2015/0005588 A1* | 1/2015 | Herken ............... G10L 25/48 600/509 |
| 2015/0018598 A1* | 1/2015 | Nabutovsky ....... A61N 1/36071 607/101 |
| 2016/0271384 A1* | 9/2016 | Kaib ............... A61N 1/0492 |
| 2019/0160278 A1 | 5/2019 | Volosin et al. |
| 2019/0298987 A1* | 10/2019 | Freeman ............... A61N 1/08 |
| 2020/0101278 A1 | 4/2020 | Freeman et al. |
| 2020/0282225 A1* | 9/2020 | Kumar ............... A61N 1/046 |

(56) References Cited

U.S. PATENT DOCUMENTS

2021/0106811 A1    4/2021   Quinnell et al.
2023/0131320 A1    4/2023   Quinnell et al.

FOREIGN PATENT DOCUMENTS

| EP | 0295497 | B1 | 9/1993 |
| EP | 0335356 | B1 | 3/1996 |
| EP | 1455640 | B1 | 1/2008 |
| EP | 2083104 | A2 | 7/2009 |
| EP | 1720446 | B1 | 7/2010 |
| JP | 5115450 | A | 5/1993 |
| JP | 2006510431 | A | 3/2006 |
| JP | 2006512128 | A | 4/2006 |
| JP | 2006223168 | A | 8/2006 |
| JP | 2009510276 | A | 3/2009 |
| WO | 200002484 | A1 | 1/2000 |
| WO | 2004054656 | A1 | 7/2004 |
| WO | 2006050235 | A1 | 5/2006 |
| WO | 20070057169 | A1 | 5/2007 |
| WO | 2007077997 | A1 | 7/2007 |
| WO | 2015056262 | A1 | 4/2015 |
| WO | 2016149450 | A1 | 9/2016 |

OTHER PUBLICATIONS

DeBock et al., "Captopril treatment of chronic heart failure in the very old," J. Gerontol. (1994) 49: M148-M152.
http://www.web.archive.org/web/20030427001846/http:/www.lifecor.com/imagelib/imageproduct.asp. Published by LifeCor, Inc., 2002, on a webpage owned by LifeCor, Inc.
O'Keeffe et al., "Reproducability and responsiveness of quality of the assessment and six minute walk test in elderly heart failure patients," Heart (1998) 80: 377-382.

* cited by examiner

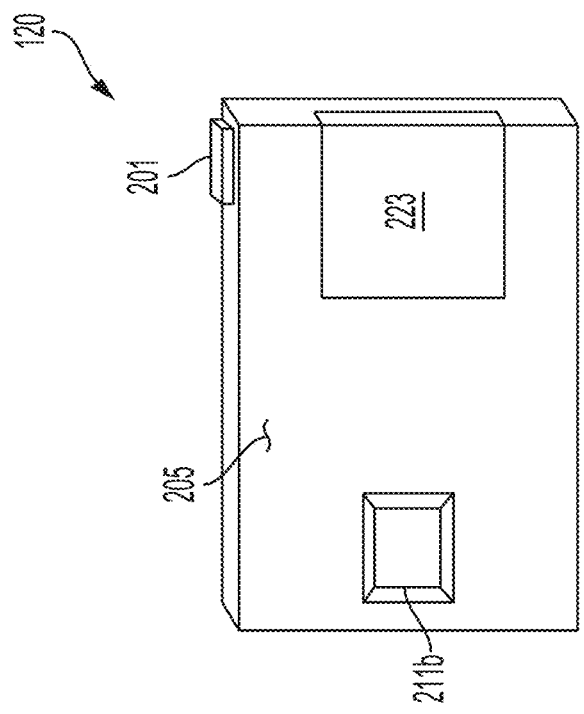
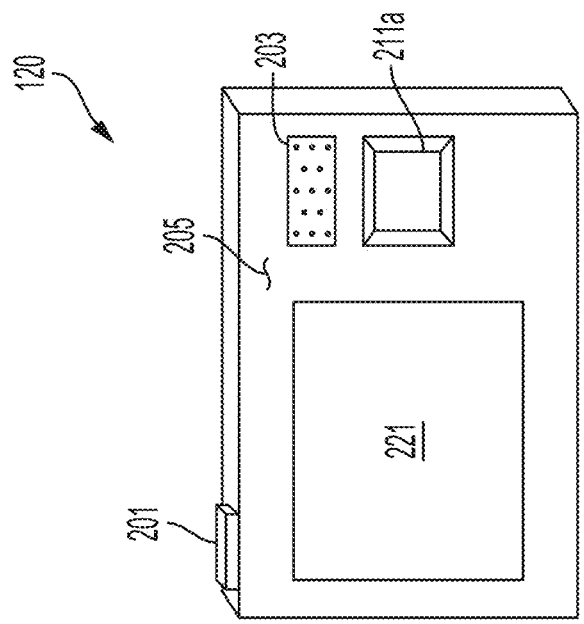
FIG. 2A
FIG. 2B

MODULAR INGRESS PROTECTED ELECTRODE SYSTEM FOR A WEARABLE DEFIBRILLATOR

CROSS-REFERENCE TO RELATED APPLICATIONS

This application claims priority under 35 U.S.C. § 119(e) to U.S. Provisional Patent Application Ser. No. 63/146,763, titled "MODULAR INGRESS PROTECTED ELECTRODE SYSTEM FOR A WEARABLE DEFIBRILLATOR," filed Feb. 8, 2021, the contents of which being incorporated herein in their entirety for all purposes.

BACKGROUND

The present disclosure is generally directed to systems and methods of delivering electrical therapy to a subject.

There are a wide variety of electronic and mechanical devices for monitoring and treating subjects' medical conditions. In some examples, depending on the underlying medical condition being monitored or treated, medical devices such as cardiac monitors or defibrillators may be surgically implanted or externally connected to the subject. In some examples, physicians may use medical devices alone or in combination with drug therapies to treat conditions such as cardiac arrhythmias.

One of the deadliest cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a subject in which various arrhythmias of the heart, such as ventricular fibrillation, ventricular tachycardia, pulseless electrical activity (PEA), and asystole (e.g., heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the subject. The sooner these resuscitation efforts begin, the better the subject's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the subject's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the subject's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus™ also available from ZOLL Medical Corporation.

Some examples of cardiac monitoring and/or treatment devices include therapy electrodes that release conductive gel onto the skin of a subject prior to delivering electrical therapy to the subject to decrease electrical resistance between the therapy electrode and the subject. Such therapy electrodes have in the past been single use devices that would be replaced after each use with the used devices being discarded.

SUMMARY

In accordance with one aspect, there is provided a modular waterproof therapeutic electrode component for preventing water ingress and for easy servicing. The component comprises a substrate comprising a conductive surface, a reservoir of conductive fluid mounted on the substrate, a reusable waterproof enclosure comprising circuitry, the reusable waterproof enclosure comprising circuitry configured to be removably coupled to the substrate, and a fluid deployment device in electrical communication with the circuitry and mounted on the substrate, the fluid deployment device configured to cause the reservoir to release the conductive fluid onto the conductive surface to reduce electrical impedance between the conductive surface and skin of a subject.

In some embodiments, the fluid deployment device includes a gas generator configured to supply pressurized gas to the reservoir.

In some embodiments, the fluid deployment device includes an air pump configured to supply pressurized air to the reservoir.

In some embodiments, the fluid deployment device includes a pressurized working fluid source configured to supply pressurized working fluid to the reservoir.

In some embodiments, the conductive surface is a lower surface of the substrate and the reusable waterproof enclosure is configured to be removably coupled to an upper surface of the substrate.

In some embodiments, the reusable waterproof enclosure is configured to be removably coupled to a mounting plate disposed on the substrate, the mounting plate providing a conduction path for high voltage electrical therapy from the circuitry to the conductive surface.

In some embodiments, the mounting plate includes press fit pins configured to make contact with electrical contacts in the circuit board when the reusable waterproof enclosure is coupled t the substrate.

In some embodiments, the fluid deployment device and reservoir of conductive fluid are disposed on the upper surface of the substrate.

In some embodiments, the reusable waterproof enclosure is configured to be removably coupled to a interconnect board disposed on the substrate, the interconnect board including a board-to-board connector that mates with a complimentary connector in the circuitry and that provides a conduction path for high voltage electrical therapy from the circuitry to the conductive surface.

In some embodiments, the component further comprises a waterproof high voltage electrical connector extending from the circuitry and beyond the reusable waterproof enclosure, the waterproof high voltage electrical connector removably electrically connectable to the conductive surface of the substrate for delivering electrical stimulus to the subject.

In some embodiments, the component further comprises a waterproof fluid deployment device connector extending from the circuitry and beyond the reusable waterproof enclosure, the waterproof fluid deployment device connector having a first portion including first electrical conductors extending from the circuitry for delivering an activation signal to the fluid deployment device, and a second portion of the waterproof fluid deployment device connector mechanically engageable with and mechanically disengageable from the first portion, the second portion including second electrical conductors extending to the fluid deployment device for delivering the activation signal to the fluid deployment device.

In some embodiments, the waterproof enclosure, waterproof high voltage electrical connector, and waterproof fluid deployment device connector each has a liquid ingress protection rating of at least one of IPX3, IPX4, IPX5, IPX6, IPX7, or IPX8 as specified in international standard EN 60529 (British BS EN 60529:1992, European IEC 60509: 1989).

In some embodiments, the reusable waterproof enclosure has a solid particle ingress protection rating of one of IP3X, IP4X, IP5X, or IP6X as specified in international standard EN 60529 (British BS EN 60529:1992, European IEC 60509:1989).

In accordance with another aspect, there is provided a modular waterproof therapeutic electrode component for preventing water ingress and for easy servicing. The component comprises a substrate comprising a conductive lower surface, a reservoir of conductive fluid mounted on the substrate opposite the conductive lower surface, a gas generator also mounted on the substrate, the gas generator configured to supply pressurized gas to the reservoir and cause the reservoir to release the conductive fluid onto the conductive lower surface to reduce electrical impedance between the conductive lower surface and skin of the subject, a circuit board encapsulated within a waterproof enclosure, the waterproof enclosure removably coupled to the substrate, a waterproof high voltage electrical connector extending from the circuit board and beyond the waterproof enclosure, the waterproof high voltage electrical connector removably electrically connectable to the conductive lower surface of the substrate for delivering the electrical stimulus to the subject, and a waterproof gas generator connector extending from the circuit board and beyond the waterproof enclosure, the waterproof gas generator connector having a first portion including first electrical conductors extending from the circuit board for delivering an activation signal to the gas generator, and a second portion of the waterproof gas generator connector mechanically engageable with and mechanically disengageable from the first portion, the second portion including second electrical conductors extending to the gas generator for delivering the activation signal to the gas generator.

In some embodiments, the waterproof enclosure, waterproof high voltage electrical connector, and waterproof gas generator connector has a liquid ingress protection rating of at least one of IPX3, IPX4, IPX5, IPX6, IPX7, or IPX8 as specified in international standard EN 60529 (British BS EN 60529:1992, European IEC 60509:1989).

In some embodiments, the waterproof enclosure has a solid particle ingress protection rating of one of IP3X, IP4X, IP5X, or IP6X as specified in international standard EN 60529 (British BS EN 60529:1992, European IEC 60509: 1989).

In some embodiments, the waterproof enclosure of the circuit board comprises a solid overmolding formed of a waterproof thermoplastic material.

In some embodiments, the solid overmolding is disposed within a sealed housing comprising the thermoplastic material filled within the sealed housing.

In some embodiments, the component further comprises a mounting plate disposed on the substrate and including threaded fittings, the sealed housing including a plurality of apertures providing for fasteners to pass through the sealed housing and engage the threaded fittings of the mounting plate to secure the sealed housing to the substrate.

In some embodiments, the mounting plate is a conductive plate electrically connected to the conductive lower surface of the substrate and wherein the waterproof high voltage electrical connector includes one or more pins extending from the mounting plate and configured to engage respective electrical contacts disposed on the circuit board when the sealed housing is secured to the substrate.

In some embodiments, the component further comprises a gasket disposed on the mounting plate around the one or more pins to provide liquid ingress protection of at least one of IPX3, IPX4, IPX5, IPX6, IPX7, or IPX8 between the substrate and the sealed housing board when the sealed housing is secured to the substrate.

In some embodiments, the component further comprises an interconnect board captured within the mounting plate and including high voltage conductive traces electrically connected to the conductive lower surface of the substrate, the waterproof high voltage electrical connector including one or more pins extending from the interconnect board and configured to engage respective electrical contacts disposed on the circuit board when the sealed housing is secured to the substrate, the high voltage conductive traces and high voltage electrical connector capable of withstanding voltages of between 1000 volts and 3500 volts and currents of between 1 ampere and 250 amperes.

In some embodiments, the component further comprises comprising a flexible circuit disposed on the substrate and including a high voltage conductive trace electrically connected to the conductive lower surface of the substrate, the waterproof high voltage electrical connector including one or more pins extending from the flexible circuit and configured to engage respective electrical contacts disposed on the circuit board when the sealed housing is secured to the substrate.

In some embodiments, the waterproof gas generator connector has an ingress protection rating of at least one of IP66, IP67, or IP68 as defined in international standard EN 60529 (British BS EN 60529:1992, European IEC 60509:1989).

In some embodiments, the waterproof high voltage electrical connector is included in a same connector housing as the waterproof gas generator connector.

In some embodiments, the first portion of the waterproof gas generator connector is mechanically engageable with and mechanically disengageable from the second portion of the waterproof gas generator connector by a snap fit connection.

In some embodiments, the component further comprises a seal disposed one or both of respective engagement faces of the first portion of the waterproof gas generator connector and the second portion of the waterproof gas generator connector to increase a degree of water ingress protection of the waterproof gas generator connector.

In some embodiments, the waterproof high voltage electrical connector includes a conductive lead electrically connected to a conductive tab disposed on the substrate that is electrically connected to the conductive lower surface of the substrate.

In some embodiments, the conductive lead is electrically connected to the conductive tab with solder to allow the conductive lead to be disconnected from the conductive tab by melting the solder.

In some embodiments, the conductive lead terminates in a pin that is connected to the conductive tab via a soldered crimp connection.

In some embodiments, the component is disposed in a garment wearable on a torso of the subject.

In some embodiments, the component is disposed in the garment along with electrocardiogram (ECG) electrodes for detecting an ECG of the subject.

In some embodiments, the component is disposed in the garment along with a monitor/controller for receiving ECG signals from the ECG electrodes and detecting arrhythmias.

In some embodiments, the component is disposed in the garment along with user interface to warn the subject of an impending electrical stimulus to be delivered to the subject via the component, the user interface providing for the subject to respond to the warning to abort delivery of the electrical stimulus.

In accordance with another aspect, there is provided a wearable therapeutic device including modular waterproof components for easy servicing after use in a wearable medical device for application of electrical stimulus to a subject. The device comprises a plurality of modular waterproof therapeutic electrode components, at least one of the plurality of modular waterproof therapeutic electrode components including a substrate comprising a conductive lower surface, a reservoir of conductive fluid mounted on the substrate opposite the conductive lower surface, a gas generator also mounted on the substrate, the gas generator configured to supply pressurized gas to the reservoir and cause the reservoir to release the conductive fluid onto the conductive lower surface to reduce electrical impedance between the conductive lower surface and skin of the subject, a circuit board encapsulated within a waterproof enclosure, the waterproof enclosure and removably coupled to the substrate, a waterproof high voltage electrical connector extending from the circuit board and beyond the waterproof enclosure, the waterproof high voltage electrical connector removably electrically connectable to the conductive lower surface of the substrate for delivering the electrical stimulus to the subject, and a waterproof gas generator connector extending from the circuit board and beyond the waterproof enclosure, the waterproof gas generator connector having a first portion including first electrical conductors extending from the circuit board for delivering an activation signal to the gas generator, and a second portion of the waterproof electrical connector mechanically engageable with and mechanically disengageable from the first portion, the second portion including second electrical conductors extending to the gas generator for delivering the activation signal to the gas generator, a waterproof distribution node including waterproof electrical connectors, and a wiring harness having waterproof electrical connectors removably connectable to the waterproof electrical connectors of the distribution node for providing electrical communication between the distribution node and each of the plurality of modular waterproof therapeutic electrode components.

In some embodiments, the component is at least one of the plurality of modular waterproof therapeutic electrode components includes an electrical passthrough to deliver electrical signals and an electrical stimulus pulse from the distribution node to another of the plurality of modular waterproof therapeutic electrode components.

In some embodiments, each of the plurality of modular waterproof therapeutic electrode components and waterproof distribution node are disposed in a garment to be worn on a torso of the subject.

In some embodiments, the plurality of modular waterproof therapeutic electrode components and waterproof distribution node are disposed in the garment along with electrocardiogram (ECG) electrodes for detecting an ECG of the subject, and wherein the waterproof electrical connectors of the waterproof distribution node include an electrical connector configured to provide electrical communication between the ECG electrodes and the waterproof distribution node.

In some embodiments, the device is disposed in the garment along with a monitor/controller for receiving ECG signals from the ECG electrodes and detecting arrhythmias.

In some embodiments, the device is disposed in the garment along with user interface to warn the subject of an impending electrical stimulus to be delivered to the subject via the plurality of modular waterproof therapeutic electrode components, the user interface providing for the subject to respond to the warning to abort delivery of the electrical stimulus.

In some embodiments, the waterproof distribution node is encapsulated in a solid overmolding formed of a waterproof thermoplastic material.

In some embodiments, the waterproof electrical connectors of the distribution node includes more than one connector configured to provide communication with more than one respective modular waterproof therapeutic electrode component through the wiring harness, more than one connector configured to provide communication with ECG electrodes, and a connector configured to provide communication with a monitor/controller of the device.

In some embodiments, the waterproof enclosure is configured to be removably coupled to an upper surface of the substrate.

In some embodiments, the gas generator is disposed on the upper surface of the substrate.

In some embodiments, the waterproof enclosure, waterproof high voltage electrical connector, and waterproof gas generator connector each has a liquid ingress protection rating of at least one of IPX3, IPX4, IPX5, IPX6, IPX7, or IPX8 as specified in international standard EN 60529 (British BS EN 60529:1992, European IEC 60509:1989).

In some embodiments, the waterproof enclosure has a solid particle ingress protection rating of one of IP3X, IP4X, IP5X, or IP6X as specified in international standard EN 60529 (British BS EN 60529:1992, European IEC 60509:1989).

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 2A depicts a first view of a medical device controller for the wearable medical device of FIG. 1;

FIG. 2B depicts a second view of a medical device controller for the wearable medical device of FIG. 1;

DETAILED DESCRIPTION

Figure 1:
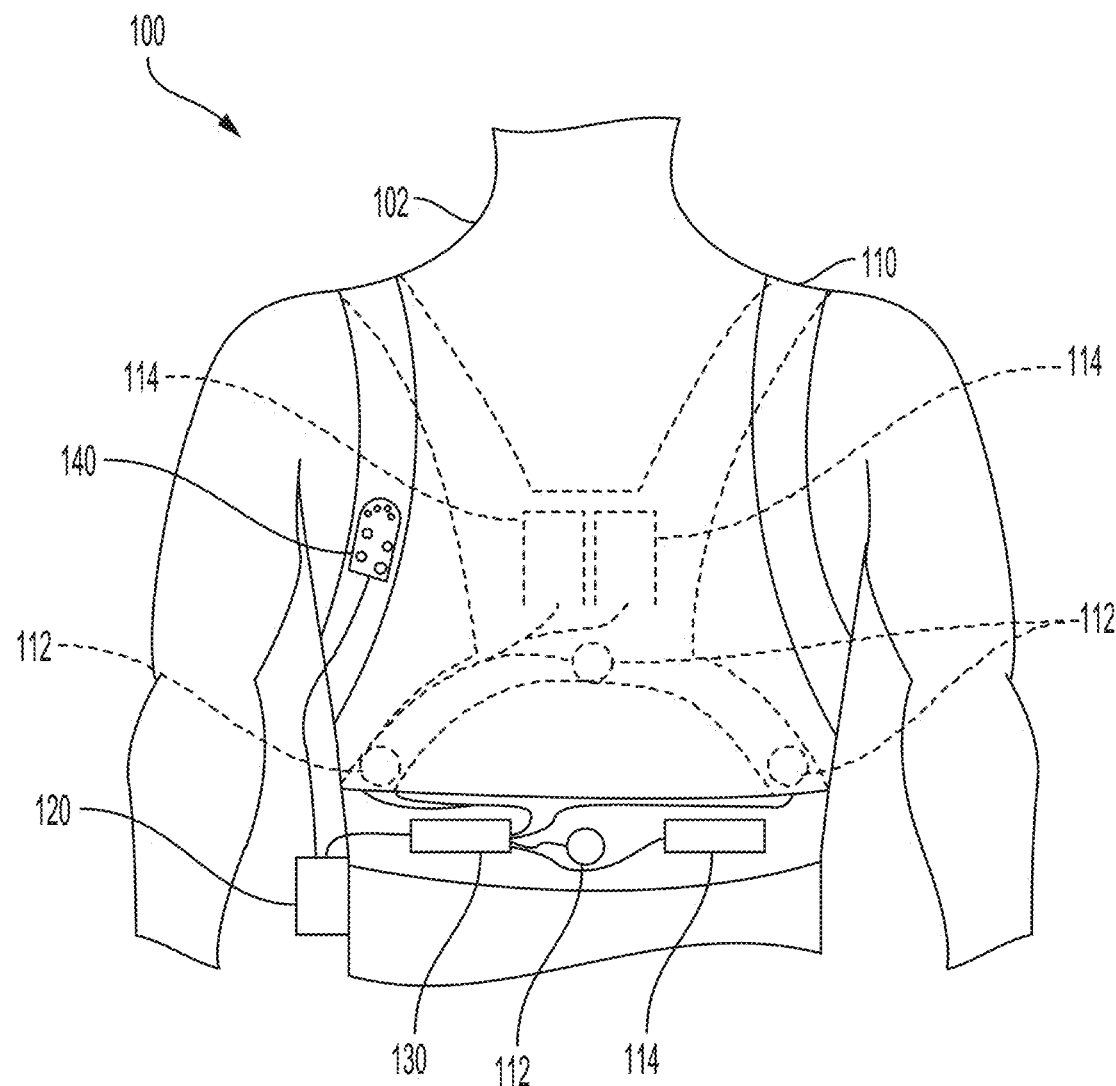
FIG. 1 depicts an example of a wearable medical device.

This disclosure relates to devices, systems and methods for delivering electrical therapy to a subject.

Cardiac monitoring and/or treatment systems may include therapy electrode components that release conductive fluid or gel onto the skin of a subject prior to delivering electrical therapy. The gel causes a decrease in electrical resistance between the conductive surface of the therapy electrode and the subject's skin. The deployed gel can help avoid causing burns on the subject's skin during therapy. Further, the deployed gel can cause substantially all or most of the current from the therapeutic electrode components to be delivered to the subject. In implementation, the conductive fluid or gel may have a limited shelf life, for example, due to evaporation of liquid from the conductive fluid or gel. For example, such evaporation can occur through the walls of the receptacle(s) in the therapy electrode components that house the conductive fluid or gel prior to dispensing the fluid or gel. Example devices, systems, and methods are described herein to allow for reuse of components of a therapeutic device/cardiac monitoring/treatment system (hereinafter, a therapeutic device system). For example, during service, the deteriorated conductive fluid or gel, or a component including the conductive fluid or gel, can be removed and the remaining therapeutic device system components can be reused with new components including conductive fluid or gel.

As described further below, a non-limiting list of components of the therapeutic device system that are designed herein to be re-used include a wiring harness and associated circuit boards and sensors. The circuit boards may include, for example, a central control or distribution node and circuit boards configured to control activation of a fluid deployment device or gel release mechanism, for example, a gas cartridge or air or fluid pump, in a therapy electrode, as well as to control delivery of electrical therapy to a subject through therapy electrodes of the system. In instances in which, for example, the conductive fluid or gel in a therapy electrode component reaches or exceeds its shelf life or if the therapy electrode component or fluid deployment device develops a leak or some other defect that would warrant replacement of the therapy electrode component, the therapy electrode component may be discarded. Example devices, systems, and methods are described herein to allow for reuse of the remaining portions of the therapeutic device system, for example, wiring harness, circuit boards and sensors with replacement therapy electrode components.

Implementations herein also provide waterproof features to provide for a subject to wear the therapeutic device system while bathing or showering. Such implementations allow for subjects to be protected in the event they experience a cardiac event while bathing or showering. Accordingly, aspects and embodiments disclosed herein include therapeutic device systems that are at least partially waterproof or in some instances sufficiently waterproof to be worn by a subject while bathing or showering to provide continuous monitoring or availability of electrical therapy to the subject. Further, aspects and embodiments disclosed herein include therapeutic device systems that are resistant to the ingress of particulate matter that might otherwise potentially damage components of the system.

Examples of devices and systems for delivering externally-applied electrical therapy to a subject disclosed herein include a therapeutic electrode component for application of transcutaneous electrical stimuli such as transcutaneous pacing stimuli or transcutaneous defibrillation and/or cardioversion stimuli to a subject. The systems include multiple components that may be reused with replacement portions of therapeutic electrode components should replacement of one or more portions of one or more therapeutic electrode components be warranted. The therapy electrode components may be modular, waterproof, and easily serviceable by a subject or medical personnel.

In examples, the therapeutic electrode component includes a base plate or substrate having a first side (e.g., an upper side) and a second side (e.g., a lower side) opposing the first side. The second side of the therapeutic electrode component has a conductive surface that is to be disposed directly in contact with the skin of a subject, or indirectly such as through clothing, fabric, and/or a conductive mesh. The conductive surface may be disposed against, for example, a portion of the chest or back of the subject. Electrical therapy may be delivered to the subject through the conductive surface. The first side of the base plate includes a repository having an internal volume configured to releasably retain a conductive fluid or gel that is expelled onto the skin of the subject and provides a low impedance electrical path between the conductive surface of the base plate and the skin of the subject to facilitate the delivery of the electrical therapy to the subject. A rupturable membrane is disposed between the internal volume of the repository and the conductive surface of the base plate which ruptures in response to pressure applied to the conductive fluid and allows the conductive fluid to be expelled onto the skin of the subject.

In implementations herein, a coupling is disposed on the base plate that allows one to detachably engage a waterproof enclosure or casing with the base plate, the waterproof enclosure or casing comprising circuitry. The circuitry is used to control a fluid deployment device (e.g., gas cartridge, air or fluid pump) to provide pressure to the conductive fluid when it is desired to expel the conductive fluid onto the skin of the subject and to control delivery of therapeutic electrical shocks to a subject. For example, the circuitry includes one or more microprocessors encoded with instructions to control the delivery of the conductive fluid based on a determination that the patient is undergoing a life-threatening cardiac arrhythmia Examples of such life-threatening cardiac arrhythmias may be paceable conditions such as bradycardia, tachycardia, or asystole, or conditions treatable by defibrillation or cardioversion such as ventricular tachycardia or ventricular fibrillation.

The casing including the circuitry is detachable from the coupling without causing destruction of at least the casing and circuitry so that the base plate and conductive gel reservoir disposed thereon may be replaced or removed when warranted and replaced with a new base plate to which the circuitry may be removably attached.

In implementations, waterproof and particle ingress resistant electrical connectors may extend from the circuitry casing to electrically couple to the fluid deployment device and conductive surface of the base plate. Objective standards for waterproof and particle ingress resistance are described in further detail below. In some examples, one or more sensors, for example, one or more acoustic sensors for measuring such parameters as heart sounds, respiration, etc. of a subject may also extend from the control circuitry modules for coupling to the base plate of a therapy electrode.

Examples of systems for delivering electrical therapy to a subject disclosed herein may include a modular waterproof therapeutic electrode component for preventing water ingress and for easy servicing. The modular waterproof therapeutic electrode component may include a substrate comprising a conductive surface, a reservoir of conductive fluid mounted on the substrate, a reusable waterproof enclosure comprising circuitry, the reusable waterproof enclosure comprising circuitry configured to be removably coupled to the substrate, and a fluid deployment device in electrical communication with the circuitry and mounted on the substrate. The fluid deployment device may be configured to cause the reservoir to release the conductive fluid onto the conductive surface to reduce electrical impedance between the conductive surface and skin of a subject.

Examples of systems for delivering electrical therapy to a subject disclosed herein may include a modular waterproof therapeutic electrode component for preventing water ingress and for easy servicing. The modular waterproof therapeutic electrode component may include a substrate comprising a conductive lower surface, a reservoir of conductive fluid mounted on the substrate opposite the conductive lower surface, and a gas generator also mounted on the substrate. The gas generator may be configured to supply pressurized gas to the reservoir and cause the reservoir to release the conductive fluid onto the conductive lower surface to reduce electrical impedance between the conductive lower surface and skin of the subject. The modular waterproof therapeutic electrode component may further include a circuit board encapsulated within a waterproof enclosure that is removably coupled or couplable to the substrate. A waterproof high voltage electrical connector may extend from the circuit board and beyond the waterproof enclosure. The waterproof high voltage electrical connector may be capable of withstanding voltages of between 1000 volts and 3500 volts and currents of between 1 ampere and 250 amperes. The waterproof high voltage electrical connector may be removably electrically connectable to the conductive lower surface of the substrate for delivering the electrical stimulus to the subject. A waterproof gas generator connector may extend from the circuit board and beyond the waterproof enclosure. The waterproof gas generator connector may have a first portion including first electrical conductors extending from the circuit board for delivering an activation signal to the gas generator, and a second portion of the waterproof gas generator connector mechanically engageable with and mechanically dis-engageable from the first portion. The second portion may include second electrical conductors extending to the gas generator for delivering the activation signal to the gas generator.

Examples of systems for delivering electrical therapy to a subject disclosed herein may include a wearable therapeutic device including modular waterproof components for easy servicing after use in a wearable medical device for application of electrical stimulus to a subject. The systems may include a plurality of modular waterproof therapeutic electrode components. At least one of the plurality of modular waterproof therapeutic electrode components includes a substrate comprising a conductive lower surface, a reservoir of conductive fluid mounted on the substrate opposite the conductive lower surface, and a gas generator also mounted on the substrate. The gas generator may be configured to supply pressurized gas to the reservoir and cause the reservoir to release the conductive fluid onto the conductive lower surface to reduce electrical impedance between the conductive lower surface and skin of the subject. The at least one of the plurality of modular waterproof therapeutic electrode components further includes a circuit board encapsulated within a waterproof enclosure that is removably coupled to the substrate. A waterproof high voltage electrical connector may extend from the circuit board and beyond the waterproof enclosure. The waterproof high voltage electrical connector may be removably electrically connectable to the conductive lower surface of the substrate for delivering the electrical stimulus to the subject. A waterproof gas generator connector may extend from the circuit board and beyond the waterproof enclosure. The waterproof gas generator connector may have a first portion including first electrical conductors extending from the circuit board for delivering an activation signal to the gas generator, and a second portion of the waterproof electrical connector mechanically engageable with and mechanically dis-engageable from the first portion. The second portion may include second electrical conductors extending to the gas generator for delivering the activation signal to the gas generator. The at least one of the plurality of modular waterproof therapeutic electrode components further includes a waterproof distribution node including waterproof electrical connectors. A wiring harness having waterproof electrical connectors may be removably connectable to the waterproof electrical connectors of the distribution node for providing electrical communication between the distribution node and each of the plurality of modular waterproof therapeutic electrode components.

Advantages of various aspects and embodiments disclosed herein provide for the components of a therapy electrode component including a conductive fluid dispensation system to be non-destructively disassembled. In a therapy electrode component in which conductive fluid has expired, portions of the therapy electrode component, for example, the circuit board and/or a module housing same may be removed, and may be installed onto a replacement base portion of the therapy electrode component including fresh conductive fluid. In another example, in a therapy electrode component in which the conductive gel and other associated components, for example, the base plate, gas cartridge, conductive fluid repository, and rupturable membrane are all in useable condition, but the circuit board is in some way defective, the circuit board may be removed and replaced without damaging the base plate, gas cartridge, conductive fluid repository, and rupturable membrane. Accordingly, portions of therapy electrode components may be replaced if desired to provide a functional therapy electrode component rather than disposing and replacing the entirety of the therapy electrode component.

Aspects and embodiment disclosed herein thus provide advantages with respect to cost and with respect to the number of replacement parts a user or supplier may keep on hand to maintain the therapy electrode components of a therapy electrode system of a subject in usable or optimal condition.

As described above, the teachings of the present disclosure can be generally applied to external medical monitoring and/or treatment devices (e.g., devices that are not completely implanted within the subject's body). External medical devices can include, for example, ambulatory medical devices that are capable of and designed for moving with the subject as the subject goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device includes modular waterproof components and may be capable of continuous use by the subject. In some implementations, the continuous use can be substantially or nearly continuous in nature. That is, the wearable medical device may be continuously used, including while the subject bathes, except for sporadic periods during which the use temporarily ceases, for example, when the wearable medical device is removed for service or laundering. Such substantially or nearly continuous use as described herein may nonetheless qualify as continuous use. For example, the wearable medical device can be configured to be worn by a subject for as many as 24 hours a day. In some implementations, the subject may remove the wearable medical device for a short portion of the day (e.g., for service or cleaning).

Further, the wearable medical device can be configured as a long term or extended use medical device. Such devices can be configured to be used by the subject for an extended period of several days, weeks, months, or even years. In some examples, the wearable medical device can be used by a subject for an extended period of at least one week. In some examples, the wearable medical device can be used by a subject for an extended period of at least 30 days. In some examples, the wearable medical device can be used by a subject for an extended period of at least one month. In some examples, the wearable medical device can be used by a subject for an extended period of at least two months. In some examples, the wearable medical device can be used by a subject for an extended period of at least three months. In some examples, the wearable medical device can be used by a subject for an extended period of at least six months. In some examples, the wearable medical device can be used by a subject for an extended period of at least one year. In some implementations, the extended use can be uninterrupted until a physician or other caregiver provides specific instruction to the subject to stop use of the wearable medical device.

Regardless of the extended period of wear, the use of the wearable medical device can include continuous or nearly continuous wear by the subject as described above. For example, the continuous use can include continuous wear or attachment of the wearable medical device to the subject, e.g., through one or more of the therapy electrode components as described herein, during both periods of monitoring and periods when the device may not be monitoring the subject but is otherwise still worn by or otherwise attached to the subject. The wearable medical device can be configured to continuously monitor the subject for cardiac-related information (e.g., electrocardiogram (ECG) information, including arrhythmia information, heart sounds or heart vibrations, etc.) and/or non-cardiac information (e.g., blood oxygen, the subject's temperature, glucose levels, tissue fluid levels, and/or lung sounds or vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the subject in addition to cardiac related parameters. The wearable medical device can be configured to monitor, for example, lung vibrations (e.g., using microphones and/or accelerometers), breath vibrations, sleep related parameters (e.g., snoring, sleep apnea), tissue fluids (e.g., using radiofrequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the subject.

In implementations, an example therapeutic medical device can include an in-hospital continuous monitoring defibrillator and/or pacing device, for example, an in-hospital wearable defibrillator. In such an example, the electrodes can be adhesively attached to the subject's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the subject. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the subject's torso to deliver pacing or defibrillating therapy. Similarly, the back adhesively attachable therapy electrode attaches to the back of the subject's torso. In an example scenario, at least three ECG adhesively attachable sensing electrodes can be attached to at least above the subject's chest near the right arm, above the subject's chest near the left arm, and towards the bottom of the subject's chest in a manner prescribed by a trained professional.

A subject being monitored by an in-hospital defibrillator and/or pacing device may be confined to a hospital bed or room for a significant amount of time (e.g., 90% or more of the subject's stay in the hospital). As a result, a user interface can be configured to interact with a user other than the subject, e.g., a nurse, for device-related functions such as initial device baselining, setting and adjusting subject parameters, and changing the device batteries.

In implementations, an example of a therapeutic medical device can include a short-term continuous monitoring defibrillator and/or pacing device, for example, a short-term out-patient wearable defibrillator. For example, such a short-term out-patient wearable defibrillator can be prescribed by a physician for subjects presenting with syncope. A wearable defibrillator can be configured to monitor subjects presenting with syncope by, e.g., analyzing the subject's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the subject's skin and have a similar configuration as the in-hospital defibrillator described above.

In examples, the device can output a defibrillation therapy in the form of a biphasic pulse of between about 0 and 150 Amps. For example, the biphasic waveform is a biphasic truncated exponential waveform. The device can be programmed to provide between around 75 joules to around 150 joules (±5%) at 20° C. (68° F.) when discharged into a 50 ohm resistive load. In implementations, settings within that range can be programmable in 25 joule increments. In an implementation, the device can be configured to deliver around 35 Amps for a maximum joule defibrillating shock delivered into a 50 ohm load. In examples, the defibrillation shock sequence can include between around 1 pulse to around 10 pulses. In examples, the sequence can include around 5 pulses. If conversion of the arrhythmia occurs after a shock, the device automatically precludes delivery of remaining shocks in the sequence. With respect to pacing therapy, in implementations, a maximum current level of current waveform may be set to a value between approximately 0 mAmps to 200 mAmps. In examples, a pulse width may be set to a fixed value between approximately 0.05 ms to 2 ms. In examples, a frequency of the pulses may be set to a fixed value between approximately 30 pulses per minute (PPM) to approximately 200 PPM. In accordance with one implementation, a 40 ms square wave pulse may be used.

FIG. 1 illustrates an example of a medical device 100 that is external, ambulatory, and wearable by a subject 102, and configured to implement one or more configurations described herein. For example, the medical device 100 can be a non-invasive medical device configured to be located substantially external to the subject. Such a medical device 100 can be, for example, an ambulatory medical device that is capable of and designed for moving with the subject as the subject goes about his or her daily routine. For example, the medical device 100 as described herein can be bodily-attached to the subject such as the LifeVest® wearable cardioverter defibrillator available from ZOLL® Medical Corporation. In one example scenario, such wearable defibrillators can be worn nearly continuously or substantially continuously for two to three months at a time. During the period of time in which it is worn by the subject, the wearable defibrillator can be configured to continuously or substantially continuously monitor the vital signs of the subject and, upon determination that treatment is required, can be configured to deliver one or more therapeutic electrical pulses to the subject. For example, such therapeutic shocks can be pacing, defibrillation, cardioversion, or transcutaneous electrical nerve stimulation (TENS) pulses.

The medical device 100 can include one or more of the following: a garment 110, one or more sensing electrodes 112 (e.g., ECG electrodes), one or more therapy electrodes 114, a medical device controller 120, a connection pod 130, a subject interface pod 140, a belt, or any combination of these. In some examples, at least some of the components of the medical device 100 can be configured to be affixed to the garment 110 (or in some examples, permanently integrated into the garment 110), which can be worn about the subject's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the subject 102. The sensing electrodes 112 can be operatively coupled to the medical device controller 120 through the connection pod 130. In some implementations, the sensing electrodes 112 can be adhesively attached to the subject 102. In some implementations, the sensing electrodes 112 and at least one of the therapy electrodes 114 can be included on a single integrated patch and adhesively applied to the subject's body.

The sensing electrodes 112 can be configured to detect surface electrical activity of the subject such as electrocardiogram (ECG) signals. In certain implementations, the sensing electrodes 112 can be associated with additional components disposed within a housing of the sensing electrode 112, such as accelerometers, acoustic signal detecting devices, and other measuring devices for recording additional physiological, motion, or posture parameters. For example, such additional components can also be configured to detect other types of subject physiological parameters and acoustic signals, such as tissue fluid levels, heart vibrations, lung vibrations, respiration vibrations, subject movement, etc. Example sensing electrodes 112 include a metal electrode with an oxide coating such as tantalum pentoxide electrodes, as described in, for example, U.S. Pat. No. 6,253,099 titled "Cardiac Monitoring Electrode Apparatus and Method," the content of which is incorporated herein by reference.

In some examples, the therapy electrodes 114 can also be associated with additional components disposed on the substrate of a therapy electrode 114, and such additional components can include sensors configured to detect ECG signals as well as other physiological signals of the subject similar to those described above.

The connection pod 130 can, in some examples, include a signal processor configured to amplify, filter, and digitize the cardiac signals prior to transmitting the cardiac signals to the medical device controller 120.

One or more of the therapy electrodes 114 can be configured to deliver one or more therapeutic defibrillating shocks to the body of the subject 102 when the medical device 100 determines that such treatment is warranted based on the signals detected by the sensing electrodes 112 and processed by the medical device controller 120. Example therapy electrodes 114 can include conductive metal electrodes such as stainless-steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a subject (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a subject.

Alternatively, the optional therapeutic elements can be deactivated (e.g., by a physical or a software switch), essentially rendering the therapeutic medical device a monitoring medical device for a specific physiologic purpose or a particular subject. As an example of a software switch, an authorized person can access a protected user interface of the medical device and select a preconfigured option or perform some other user action via the user interface to deactivate the therapeutic elements of the medical device.

Figure 2C:
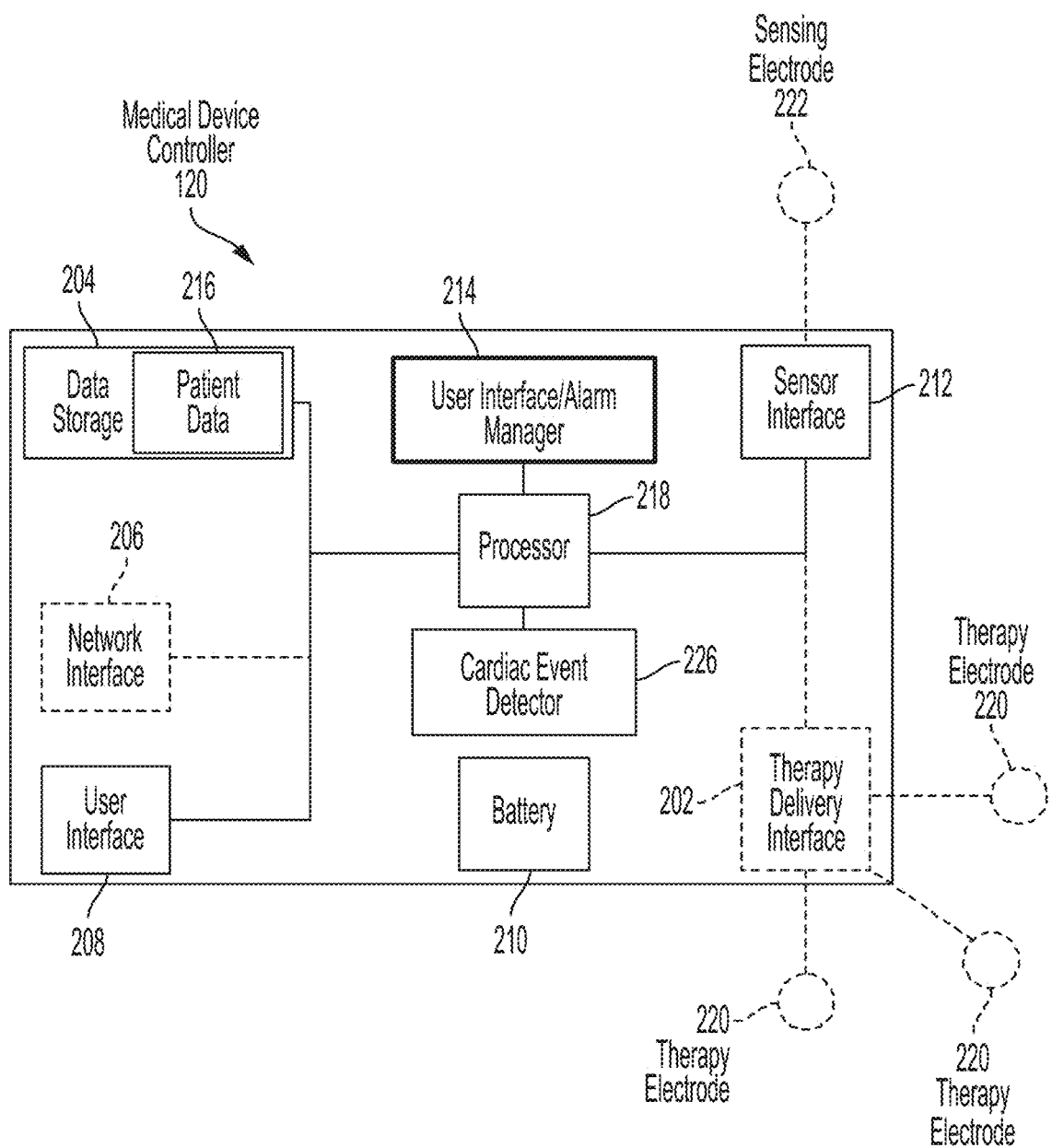
FIG. 2C depicts a component-level view of an example of a medical device controller for the wearable medical device of FIG. 1.

FIGS. 2A and 2B illustrate an example medical device controller 120. For example, the controller 120 includes a connector receptacle 201 for connecting the sensing and/or therapy electrode components to the controller 120. The controller 120 includes a speaker 203 for providing audio prompts to the subject and/or a bystander. The controller 120 includes circuitry as further described below with reference to FIG. 2C. The circuitry is housed within a mechanical housing structure 205 to protect the circuitry and other internal components of the controller 120 from physical damage, particle ingress, and/or water ingress. The controller includes one or more response buttons 211a, 211b. A subject wearing the wearable medical device can communicate with the controller 120 via the buttons 211a, 211b. For example, if the device detects a life-threatening arrhythmia condition in the subject, the controller 120 can direct the subject to press the one or more buttons 211a, 211b. In some examples, the controller 120 can include a display screen 221. For example, the display screen 221 can be a touch-sensitive panel screen responsive to subject input in the form of touch or physical force applied to the screen. For example, the display screen 221 can display controls and/or prompts to the subject and is responsive to the subject's touch or application of physical force on the displayed controls. The controller 120 can be powered by a removable battery 210 (see FIG. 2C below) that is housed within a battery chamber 223.

FIG. 2C illustrates a sample component-level view of the medical device controller 120 of the medical device 100 of FIG. 1. As shown in FIG. 2C, the medical device controller 120 can include a therapy delivery interface circuit 202, a data storage 204, a network interface 206, a user interface 208, at least one battery 210, a sensor interface 212, a user interface/alarm manager 214, and least one processor 218.

The therapy delivery interface circuit 202 can be coupled to one or more electrodes 220 configured to provide therapy to the subject (e.g., therapy electrodes 114 as described above in connection with FIG. 1). For example, the therapy delivery interface circuit 202 can include, or be operably connected to, circuitry components that are configured to generate and provide the therapeutic shock. The circuitry components can include, for example, resistors, capacitors, relays and/or switches, electrical bridges such as an H-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating subjects at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the subject's body impedance. The therapy delivery interface circuit 202 can be configured to perform the switching and pulse delivery operations, e.g., under control of the processor 218. As the energy is delivered to the subject, the amount of energy being delivered can be tracked. For example, the amount of energy can be kept to a predetermined constant value even as the pulse waveform is dynamically controlled based on factors such as the body impedance of the subject to which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the at least one processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device. The network interface 206 can include communications circuitry for transmitting data in accordance with a Bluetooth® wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1,000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the subject. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1).

The ECG electrodes 222 can monitor a subject's ECG information. For example, the ECG electrodes 222 can be galvanic (e.g., conductive) and/or capacitive electrodes configured to measure changes in a subject's electrophysiology to measure the subject's ECG information. The ECG electrodes 222 can transmit information descriptive of the ECG signals to the sensor interface 212 for subsequent analysis.

The sensor interface 212 can be coupled to any one or combination of sensing electrodes/other sensors to receive other subject data indicative of subject parameters. Once data from the sensors has been received by the sensor interface 212, the data can be directed by the at least one processor 218 to an appropriate component within the medical device controller 120. For example, if ECG data is collected by sensing electrode 222 and transmitted to the sensor interface 212, the sensor interface 212 can transmit the data to the at least one processor 218 which, in turn, relays the data to a cardiac event detector. The cardiac event data can also be stored on the data storage 204.

In certain implementations, the user interface/alarm manager 214 can be configured to manage alarm profiles and notify one or more intended recipients of events specified within the alarm profiles as being of interest to the intended recipients. These intended recipients can include external entities such as users (subjects, physicians, and monitoring personnel) as well as computer systems (monitoring systems or emergency response systems). The user interface/alarm manager 214 can be implemented using hardware or a combination of hardware and software. For instance, in some examples, the user interface/alarm manager 214 can be implemented as a software component that is stored within the data storage 204 and executed by the at least one processor 218. In this example, the instructions included in the alarm manager 214 can cause the at least one processor 218 to configure alarm profiles and notify intended recipients using the alarm profiles. In other examples, alarm manager 214 can be an application-specific integrated circuit (ASIC) that is coupled to the at least one processor 218 and configured to manage alarm profiles and notify intended recipients using alarms specified within the alarm profiles. Thus, examples of alarm manager 214 are not limited to a particular hardware or software implementation.

In some implementations, the at least one processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the at least one processor 218 can be configured to make specific logic-based determinations based on input data received, and be further configured to provide one or more outputs that can be used to control or otherwise inform subsequent processing to be carried out by the at least one processor 218 and/or other processors or circuitry with which the at least one processor 218 is communicatively coupled. Thus, the at least one processor 218 reacts to specific input stimulus in a specific way and generates a corresponding output based on that input stimulus. In some examples, the at least one processor 218 can proceed through a sequence of logical transitions in which various internal register states and/or other bit cell states internal or external to the at least one processor 218 may be set to logic high or logic low. As referred to herein, the at least one processor 218 can be configured to execute a function where software is stored in a data store coupled to the at least one processor 218, the software being configured to cause the at least one processor 218 to proceed through a sequence of various logic decisions that result in the function being executed. The various components that are described herein as being executable by the at least one processor 218 can be implemented in various forms of specialized hardware, software, or a combination thereof.

For example, the processor can be a digital signal processor (DSP) such as a 24-bit DSP processor. The at least one processor can be or include a multi-core processor, e.g., having two or more processing cores. The processor can be an Advanced RISC Machine (ARM) processor such as a 32-bit ARM processor. The at least one processor can execute an embedded operating system, and include services provided by the operating system that can be used for file system manipulation, display and audio generation, basic networking, firewalling, data encryption and communications.

Figure 3:
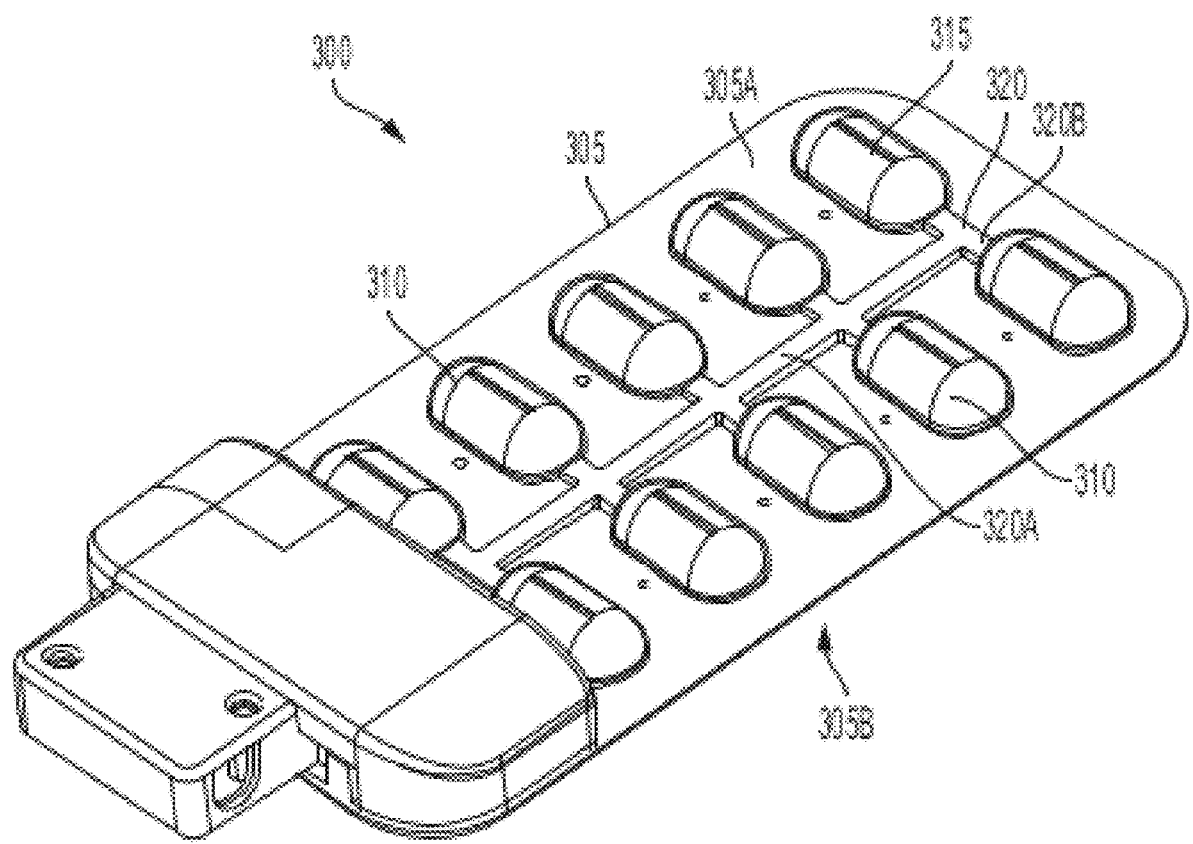
FIG. 3 depicts an example of a therapeutic electrode component.

One embodiment of a therapeutic electrode component is illustrated in FIG. 3, indicated generally as 300. The therapeutic electrode component 300 includes a base plate 305 having a first side 305A and a second side 305B opposing the first side. The second side 305B includes a conductive surface 410 (See, e.g., FIG. 7). One or more repositories 310, ten in the embodiment illustrated in FIG. 3, are disposed on the first side 305A of the base plate 305. The repositories 310 have an internal volume that releasably retains a conductive fluid 315. In examples, there may be more or fewer such repositories 310, e.g., 2-3, 10-20, 20-50, or 50-100, each carrying a predetermined quantity of the conductive fluid 315.

Figure 4:
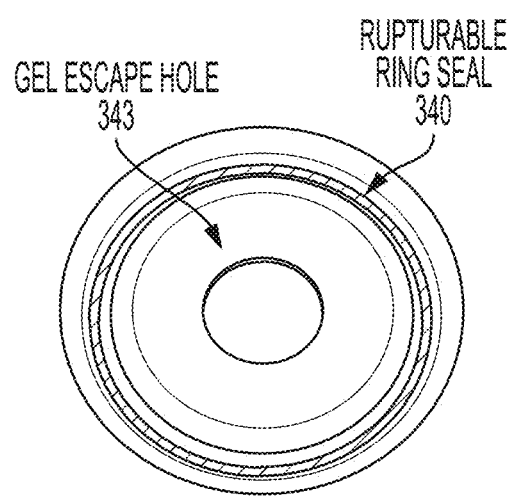
FIG. 4 depicts an example gel escape hole with a rupturable ring seal.

Referring briefly to FIG. 4, a rupturable membrane 340, e.g., in the form of a rupturable ring seal, is disposed between the internal volume of each repository 310 and the conductive surface 410 of the base plate 305. When the rupturable membrane 340 is ruptured, the fluid 315 flows from the internal volume on to the conductive surface 410 via the fluid or gel escape hole 343. The respective rupturable membranes 340 associated with each respective repository 310 are configured to rupture responsive to pressure being applied to the internal volumes of the repositories 310 so that the conductive fluid 315 can flow out of the repositories 310 and onto the conductive surface 410 of the second side 305B of the base plate 305. Each repository 310 is associated with a fluid or gel escape hole 343 to allow for the fluid or gel to escape on to the conductive surface.

Referring back to FIG. 3, a conduit 320 is disposed on the base plate 305. The conduit 320 is in fluid communication between the internal volumes of each repository 310 and a fluid deployment device, for example, a gas cartridge, air pump (See U.S. Pat. No. 10,300,266, incorporated herein by reference), or fluid pump also disposed on the base plate 305. In some embodiments, the fluid deployment device may include a pressurized working fluid source, e.g., a compressed non-noxious working fluid such as compressed nitrogen gas, compressed argon, etc., configured to supply pressurized working fluid to cause the reservoir to release the conductive fluid. Examples of such devices are disclosed in U.S. Pat. No. 10,569,090, incorporated herein by reference.

The conduit 320 includes a central portion 320A and branches 320B leading to each respective repository 310. The conduit provides for fluid to flow from the fluid deployment device to the internal volumes of the repositories 310 to pressurize the internal volumes of the repositories 310 and cause the rupturable membrane 340 to rupture and the conductive fluid 315 to be pushed out of the repositories 310 through the ruptured rupturable membrane 340 via the fluid or gel escape holes 343.

Figure 5:
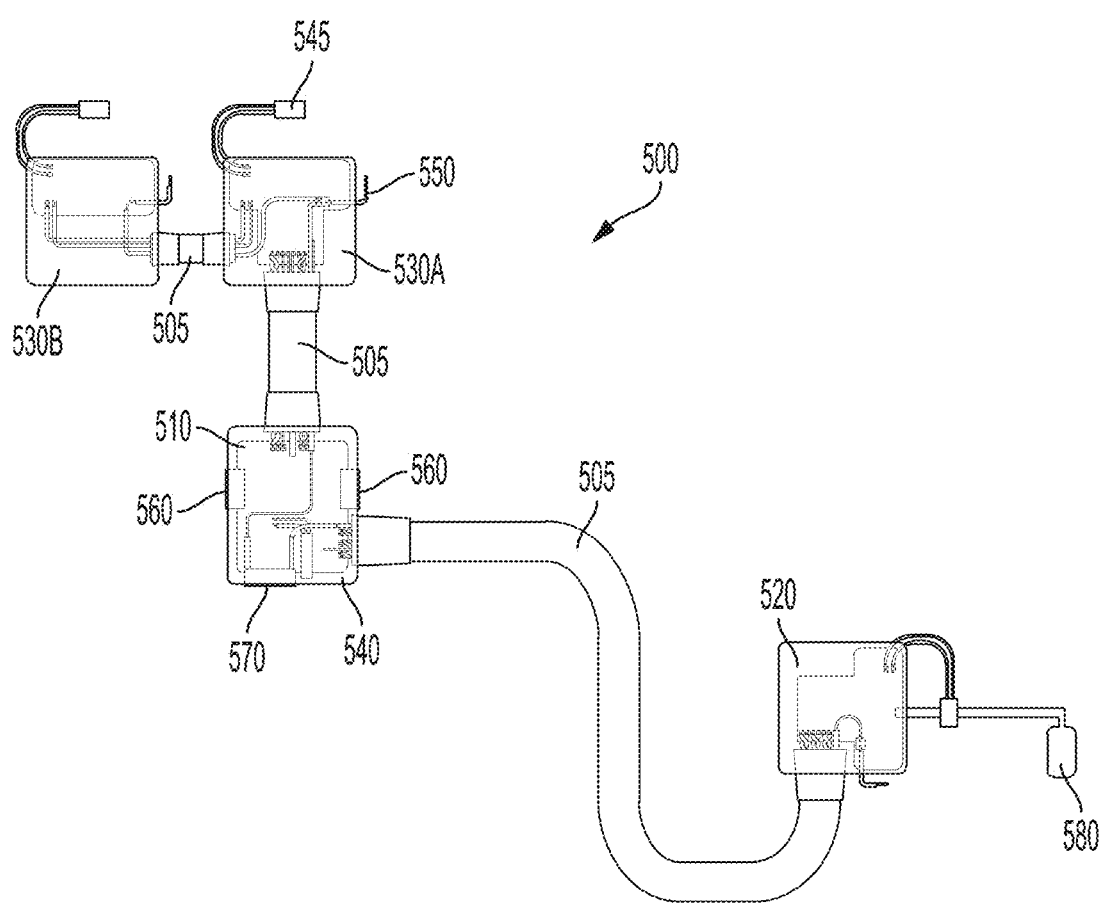
FIG. 5 depicts an example wiring harness for a wearable medical device.

A wiring harness 500 that may be utilized to electrically connect circuitry modules that may be removably coupled to substrates or base plates of examples of therapy electrodes as disclosed herein is illustrated in FIG. 5. The wiring harness 500 includes a distribution node 510, a front therapy electrode circuit board 520, and two rear therapy electrode circuit boards 530A, 530B. The distribution node 510, front therapy electrode circuit board 520, and two rear therapy electrode circuit boards 530A, 530B are hardwired 505 together. In some embodiments, a second one of the rear therapy electrode circuit boards 530B is not directly connected to the distribution node 510, but rather conductors from the distribution node 510 pass through the first one of the rear therapy electrode circuit boards 530A to the second one of the rear therapy electrode circuit boards 530B. Each of the distribution node 510, front therapy electrode circuit board 520, and two rear therapy electrode circuit boards 530A, 530B are encapsulated in waterproof enclosures 540, for example, a body of overmolding compound formed of a waterproof thermoplastic material. In some embodiments, the overmolding compound may include or consist of one of the Henkel LOCTITE® TECHNOMELT® polyamide or polyolefin thermoplastic materials, for example, TECHNOMELT® PA 6208 polyamide hotmelt adhesive.

The front therapy electrode circuit board 520 and two rear therapy electrode circuit boards 530A, 530B may include electrical leads and connectors extending from the circuit boards inside the waterproof enclosures 540 to outside of the waterproof enclosures. These electrical connectors may include waterproof fluid deployment device connectors 545 used to send signals to activate a fluid deployment device in a therapy electrode to cause release of the conductive fluid or gel, and waterproof high voltage electrical connectors 550 that electrically connect to the conductive surfaces of the therapy electrodes for delivery of electrical therapy to a subject. The waterproof fluid deployment device connectors 545 are illustrated as separate from the high voltage electrical connectors 550 in FIG. 5, but in other embodiments, as discussed below, these two connector types may be integrated into a single waterproof connector for one or more of the therapy electrode circuit boards.

In some embodiments, the waterproof enclosures 540, waterproof high voltage electrical connector 550, and waterproof fluid deployment device connector 545 each has a liquid ingress protection rating of at least one of IPX3, IPX4, IPX5, IPX6, IPX7, or IPX8 as specified in international standard EN 60529 (British BS EN 60529:1992, European IEC 60509:1989). These ingress protection ratings are defined as follows:

| Rating | Brief Description | Definition |
| --- | --- | --- |
| IPX3 | Protected against spraying water | Water sprayed at an angle up to 60° on either side of the vertical shall have no harmful effects. |
| IPX4 | Protected against splashing water | Water splashed against the enclosure from any direction shall have no harmful effects |
| IPX5 | Protected against water jets | Water projected in jets against the enclosure from any direction shall have no harmful effects |
| IPX6 | Protected against powerful water jets | Water projected in powerful jets against the enclosure from any direction shall have no harmful effects |
| IPX7 | Protected against the effects of temporary immersion in water | Ingress of water in quantities causing harmful effects shall not be possible when the enclosure is temporarily immersed in water under standardized conditions of pressure and time |

-continued

| Rating | Brief Description | Definition |
|---|---|---|
| IPX8 | Protected against the effects of continuous immersion in water | Ingress of water in quantities causing harmful effects shall not be possible when the enclosure is continuously immersed in water under conditions which shall be agreed between manufacturer and user but which are more severe than for numeral 7 |

In some embodiments, the waterproof enclosures 540 have a solid particle ingress protection rating of one of IP3X, IP4X, IP5X, or IP6X as specified in international standard EN 60529 (British BS EN 60529:1992, European IEC 60509:1989). These ingress protection ratings are defined as follows:

| Rating | Brief Description | Definition |
|---|---|---|
| IPX3 | Protected against solid foreign objects of 2.5 mm diameter and greater | The object probe, sphere of 2.5 mm diameter shall not penetrate at all |
| IPX4 | Protected against solid foreign objects of 1.0 mm diameter and greater | The object probe, sphere of 1.0 mm diameter shall not penetrate at all |
| IPX5 | Dust-protected | Ingress of dust is not totally prevented, but dust shall not penetrate in a quantity to interfere with satisfactory operation of the apparatus or to impair safety |
| IPX6 | Dust-tight | No ingress of dust. |

In some embodiments, the waterproof enclosures 540, waterproof high voltage electrical connector 550, and waterproof fluid deployment device connector 545 each has a liquid ingress protection rating of at least one of IPX3, IPX4, IPX5, IPX6, IPX7, or IPX8 as specified in international standard EN 60529 (British BS EN 60529:1992, European IEC 60509:1989) and a solid particle ingress protection rating of one of IP3X, IP4X, IP5X, or IP6X as specified in international standard EN 60529 (British BS EN 60529: 1992, European IEC 60509:1989).

The distribution node 510 may include electrical connectors 560 to which ECG electrodes may be electrically attached and an electrical connector 570 for connection to a monitor/alarm module, for example, a medical device controller 120 as illustrated in FIGS. 1-2B.

Figure 6A:
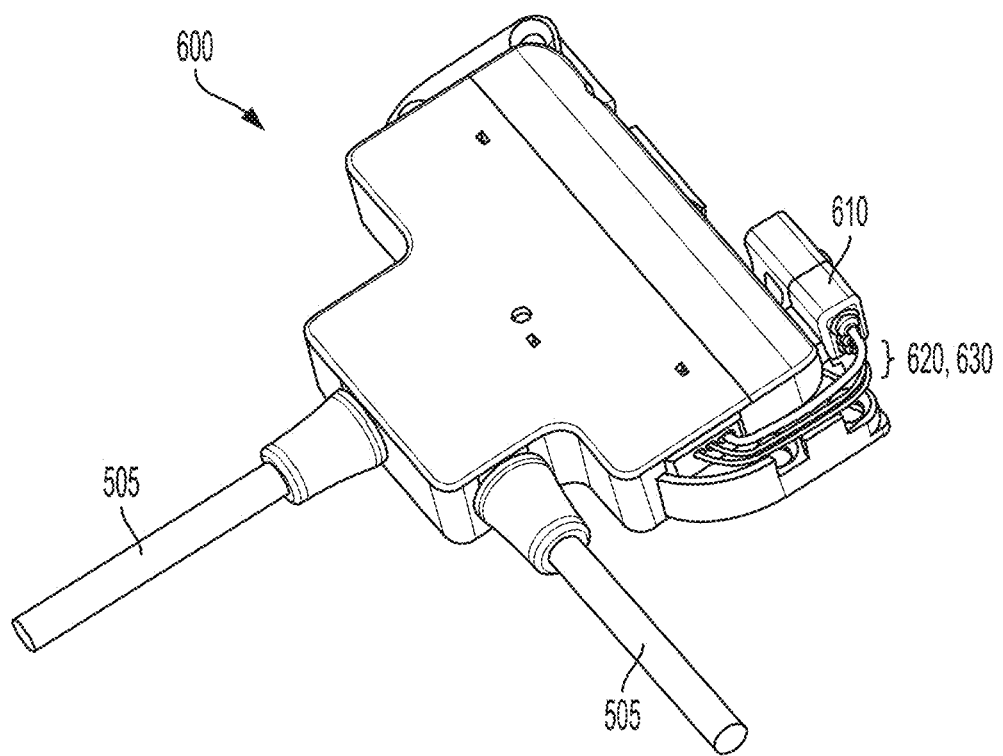
FIG. 6A depicts an example of a casing for enclosing a modular waterproof therapy electrode circuit board.

The front therapy electrode 520 may include conductors extending outward from the waterproof enclosure to a sensor 580, for example, an accelerometer or microphone for detecting heart sounds, respiration sounds, orientation, or other parameters of a subject, In addition to the waterproof enclosures 540 formed of the overmolding material, the distribution node 510, front therapy electrode circuit board 520, and two rear therapy electrode circuit boards 530A, 530B may further be enclosed within casings or enclosures formed of, for example, a plastic material such as polycarbonate that may further increase the resistance to water or particulate ingress. FIG. 6A illustrates an example of a casing 600 that may be used to house one of the overmolded front therapy electrode circuit board 520 or rear therapy electrode circuit boards 530A, 530B. The casing 600 of FIG. 6A includes two hardwired conductor cables 505 and thus may represent a casing for the overmolded rear therapy electrode circuit board 530A. A casing for the rear therapy electrode circuit board 530B or the front therapy electrode circuit board 520 may include only a single hardwired conductor cable 505. In some embodiments, the circuit boards for the therapy electrodes may be first placed within their respective casings 600 and then the overmolding material may be used to fill the space about the circuit boards within the casings and allowed to set.

Figure 7:
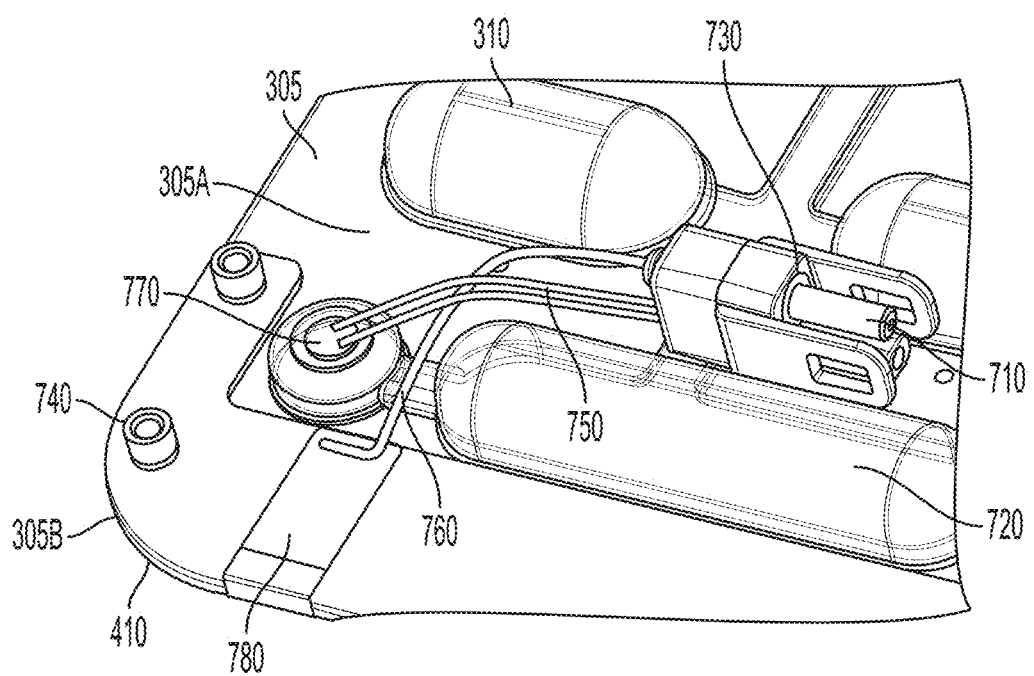
FIG. 7 illustrates wiring connections in an example of a therapy electrode.

The casing 600 illustrated in FIG. 6A includes an electrical connector 610 into which electrical conductors 620 for activation of the fluid deployment device and a high voltage electrical conductor 630 each extend. This a variation on the arrangement of the fluid deployment device electrical connector and high voltage electrical connector which are illustrated as separate in the embodiment of FIG. 5. The electrical connector 610 may be a male or female electrical connector that snap fits with a corresponding female or male electrical connector 710 disposed on a substrate or base plate 305 of a portion of a therapy electrode including a fluid deployment device 720 and gel repositories 310 as illustrated in FIG. 7. In FIG. 7, the fluid deployment device 720 is illustrated as a gas cartridge. In some embodiments, one or more seals, for example, O-rings 730 may be disposed within one or both of the electrical connectors 610, 710 to facilitate moisture and particulate ingress protection. One or more couplings or fastener receivers 740, for example, threaded receivers or PEM® nuts for receiving fasteners, for example, screws or bolts or other fasteners known in the art for securing the casing 600 to the substrate or base plate 305 may be disposed on a mounting plate 745 that may be formed of, for example, stainless steel and that is secured to the substrate or base plate 305 with, for example, an adhesive.

Figure 6B:
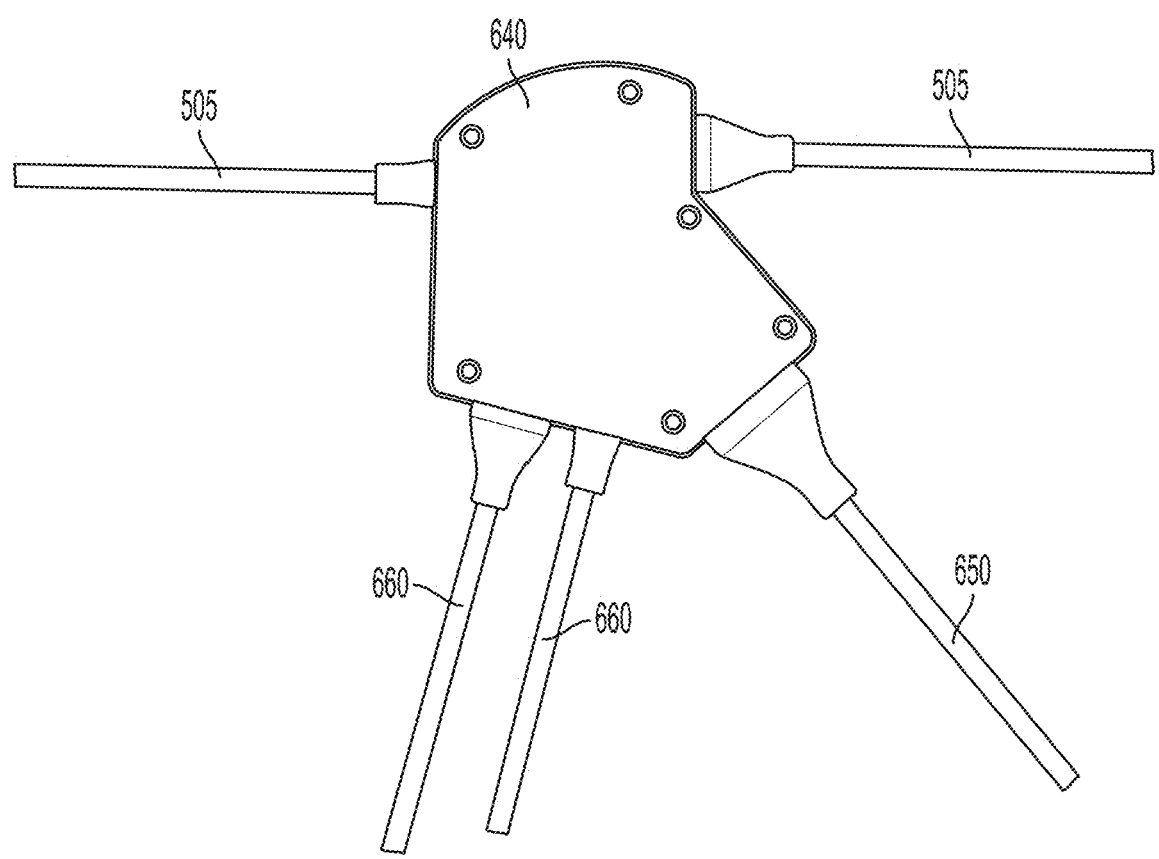
FIG. 6B depicts an example of a casing for enclosing a distribution node of a wearable medical device.

FIG. 6B illustrates an example of a casing 640 that may be used to house an overmolded distribution node, for example, distribution node 510 of FIG. 5. Hard wired conductor cables 505 extend from the casing 640 to the front and rear therapy electrode circuit boards. A removable cable 650 extends to a monitor/alarm module, for example, a medical device controller 120 as illustrated in FIGS. 1-2B. Additional removable cables 660 extend to ECG electrodes, for example ECG electrodes 112 as illustrated in FIG. 1. The locations of the different cables on the casing 640 may vary in different embodiments.

FIG. 7 illustrates how the electrical conductors 750 for activation of the fluid deployment device 720 and the electrical conductor 760 for the high voltage electricity delivery may be routed from the electrical connector 710. The electrical conductors 750 for activation of the fluid deployment device 720 extend from the electrical connector 710 and are soldered to electrical contacts 770 for the fluid deployment device 720. The electrical conductor 760 for the high voltage electricity delivery extends from the electrical connector 710 and is soldered to a conductive tab 780 formed of a metal, for example, nickel, that passes from the first side 305A (upper side) to the conductive surface 410 on the second side 305B (lower side) of the substrate or base plate 305.

Figure 8:
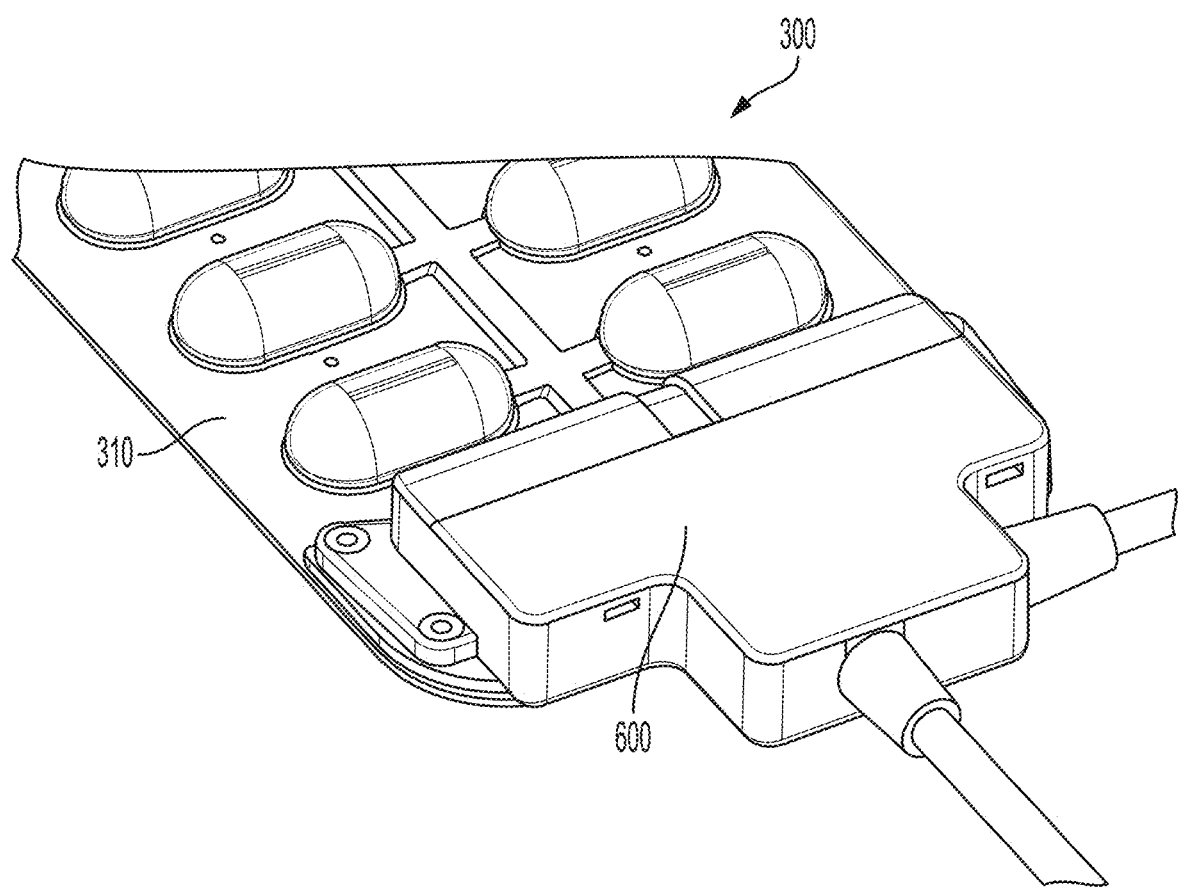
FIG. 8 depicts a therapy electrode including a casing including a circuit board mounted on the therapy electrode.
Figure 9:
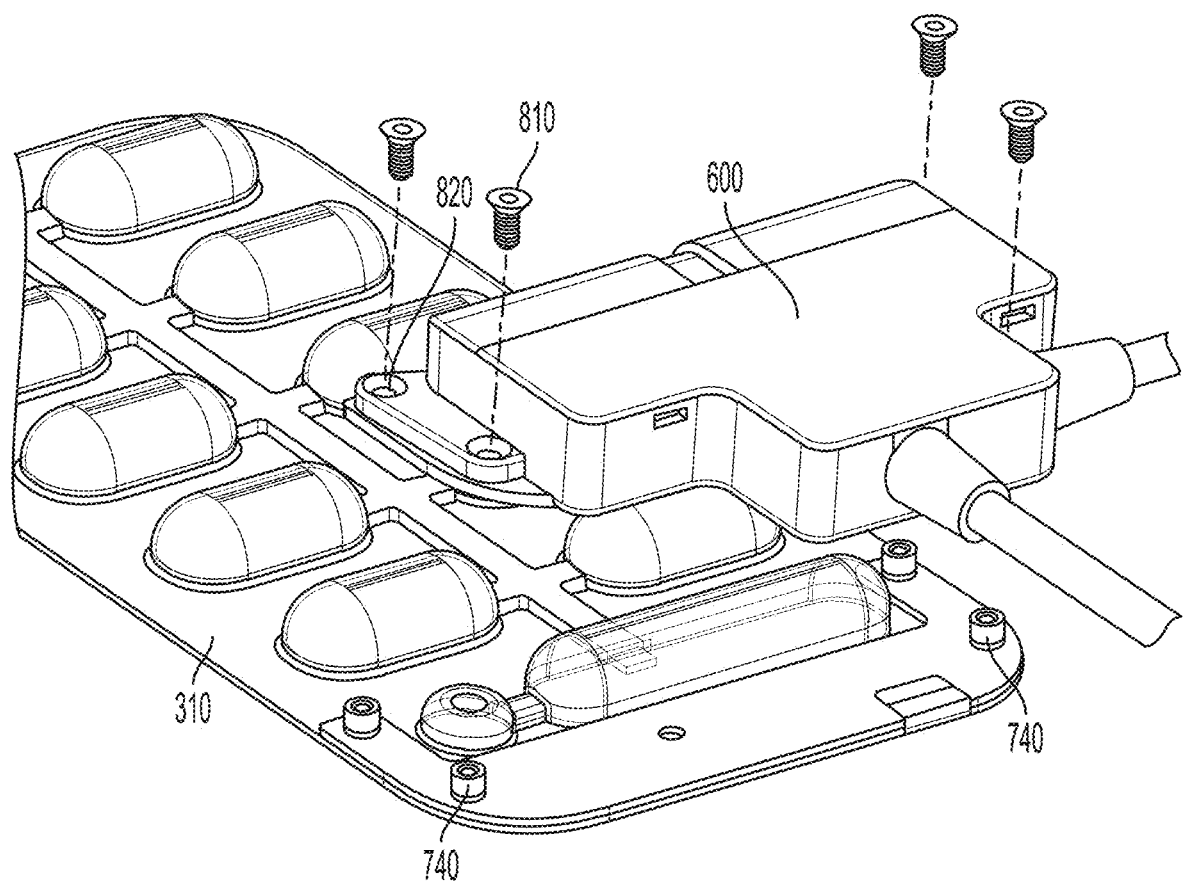
FIG. 9 depicts the therapy electrode of FIG. 8 in an exploded view with the casing detached from the base pate of the therapy electrode.

FIG. 8 illustrates an example of a housing 600 for a therapy electrode circuit board mounted on a substrate or base plate 310 of a therapy electrode 300. FIG. 9 is an exploded view of FIG. 8 showing the fasteners 810 used to removably secure the housing 600 to the substrate or base plate 310 by passing through apertures 820 in a periphery of the housing 600 and into the fastener receivers 740.

Figure 10:
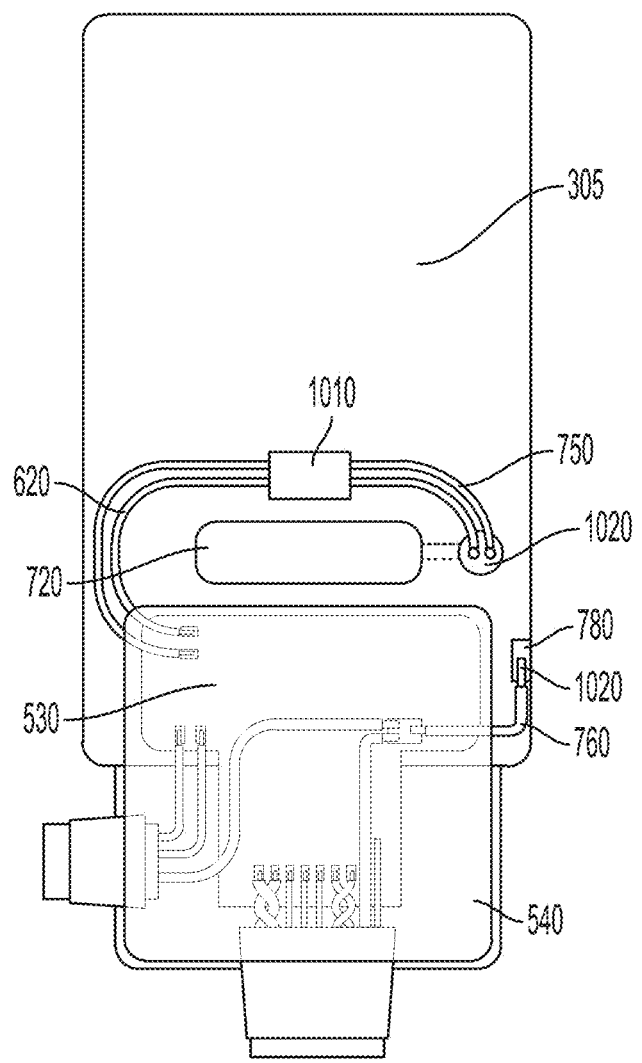
FIG. 10 depicts another example of wiring connections in an example of a therapy electrode.
Figure 11:
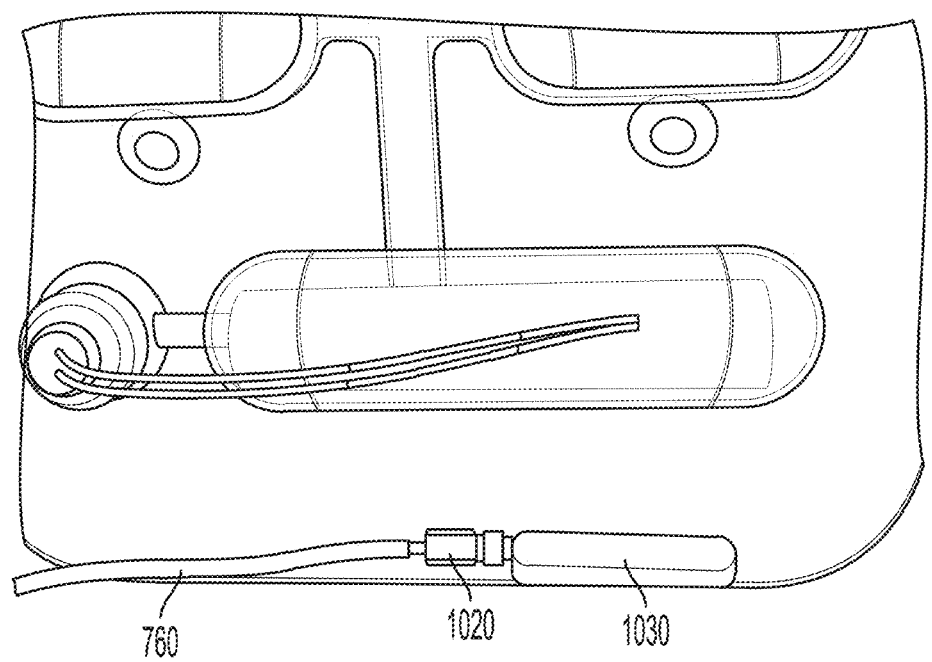
FIG. 11 depicts a crimp pin connector for a high voltage connection in an example of a therapy electrode.

An alternative embodiment of electrically connecting the electrical conductors 620/750 for activation of the fluid deployment device 720 and the electrical conductor 760 for the high voltage electricity delivery to the fluid deployment device 720 and conductive surface 410 on the second side 305B (lower side) of the substrate or base plate 305 of a therapy electrode is shown in FIG. 10. In FIG. 10 the casing 600 is not shown for sake of clarity. In the embodiment of FIG. 10, the first electrical conductors 620 for activation of the fluid deployment device 720 extend from the therapy electrode circuit board 530 and outside the waterproof enclosure 540 to a 2-position waterproof electrical connector 1010. The waterproof connector 1010 includes two portions which snap fit together, similar to connectors 610/710 described above. Second electrical conductors 750 for activation of the fluid deployment device 720 extend from the electrical connector 1010 and extend through a lead passthrough 1020 to the fluid deployment device 720 (a gas generator in FIG. 10). The electrical conductor 760 for the high voltage electricity delivery extends from the therapy electrode circuit board 530 and outside the waterproof enclosure 540 and is soldered to a conductive tab 780 formed of a metal, for example, nickel, that passes from the first side 305A (upper side) to the conductive surface 410 on the second side 305B (lower side) (not shown in FIG. 10) of the substrate or base plate 305. The end of the electrical conductor 760 that is soldered to the conductive tab 780 may be a crimp pin terminal 1020, which gets soldered to the conductive tab 780. The purpose of the crimp pin terminal is to allow multiple solder/desolder cycles so a single therapy electrode/belt node cable assembly can have the portion of the therapy electrode including the gel repositories 310 replaced many times. A bare wire lead would eventually be too short after several cycles due to the strip/tin process that would be used to make the solder joint. This problem is overcome by the crimp pin. An example of the crimp pin assembly 1030 is illustrated in FIG. 11.

Figure 12:
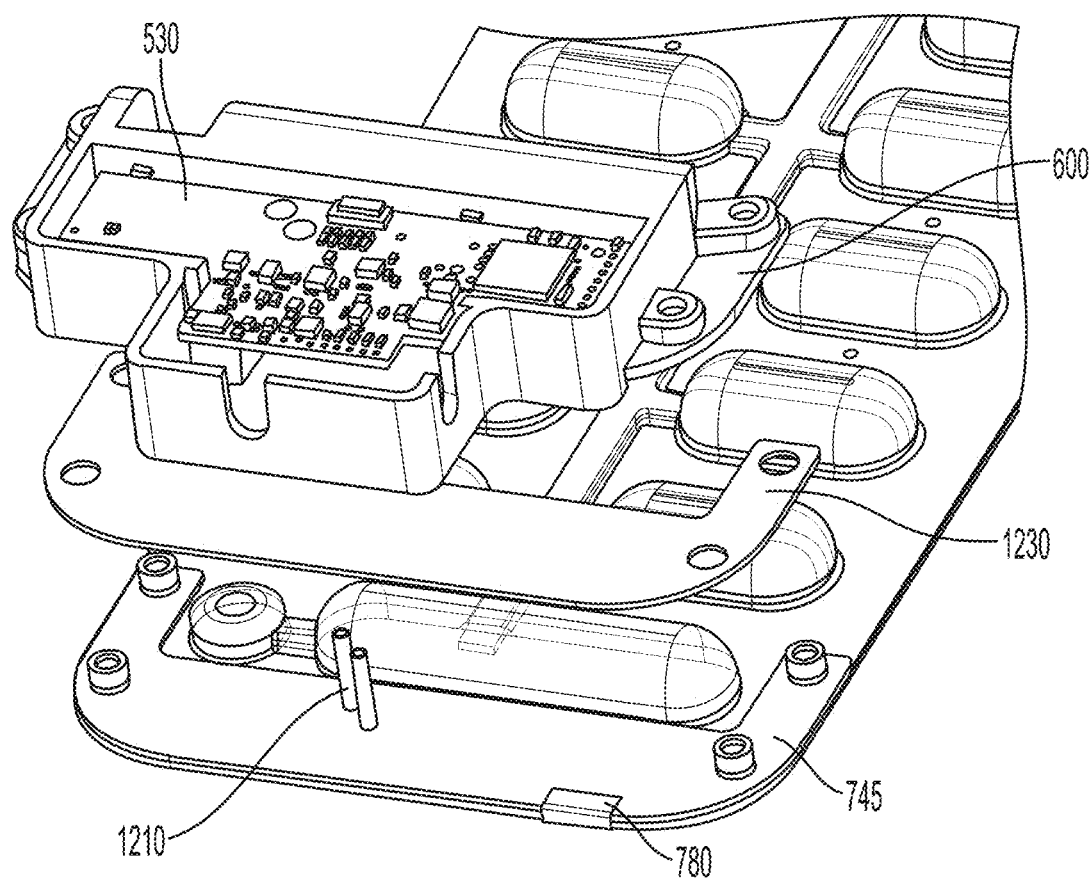
FIG. 12 depicts a therapy electrode assembly including pins for a high voltage electrical connection in an exploded view.
Figure 13:
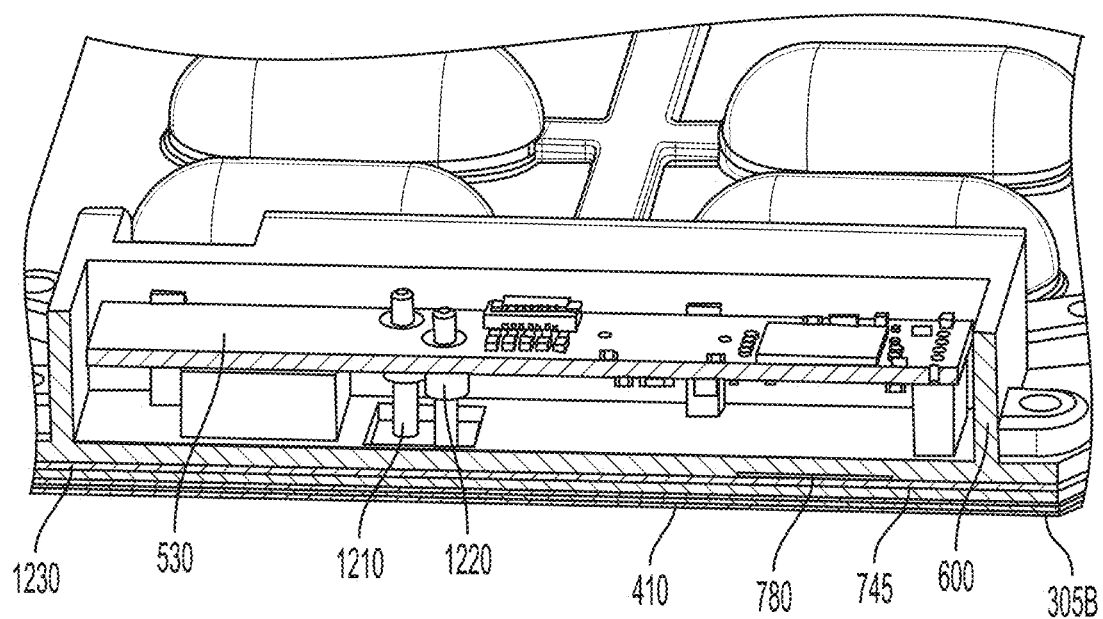
FIG. 13 is a cross section of the therapy electrode assembly of FIG. 12 in an assembled state.

In another embodiment, illustrated in FIGS. 12 and 13 a stainless steel mounting plate 745 is used as a conduction path for the high voltage electrical therapy. The conductive tab 780 from the conductive surface 410 on the second side 305B (lower side) of the substrate or base plate 305 is directly spot welded to the mounting plate 745 and two (or more) pins 1210 are press fit into the mounting plate 745. These press fit pins 1210 make contact to electrical contacts 1220 in the circuit board 530 when the casing 600 is assembled to the substrate or base plate 305. A mounting plate gasket 1230 formed of, for example, silicone may be disposed between the mounting plate 745 and substrate or base plate 305. For example, such gasket 1230 is used to keep debris out of the space between the substrate and the mounting plate 745. In this embodiment, the gas generator can be connected in a similar manner as shown in FIG. 10, e.g., using a 2-position waterproof electrical connector 1010.

Figure 14:
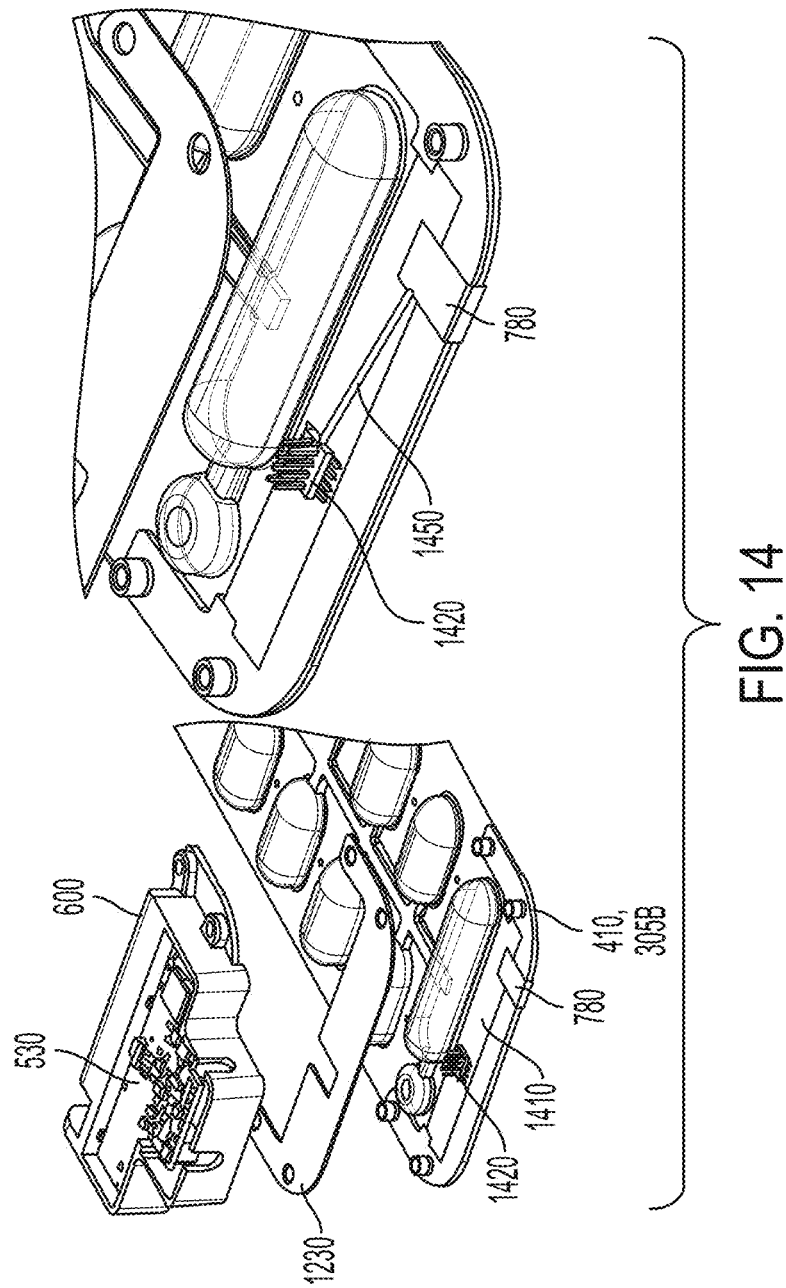
FIG. 14 illustrates a therapy electrode assembly including a board-to-board connector for a high voltage connection.
Figure 15:
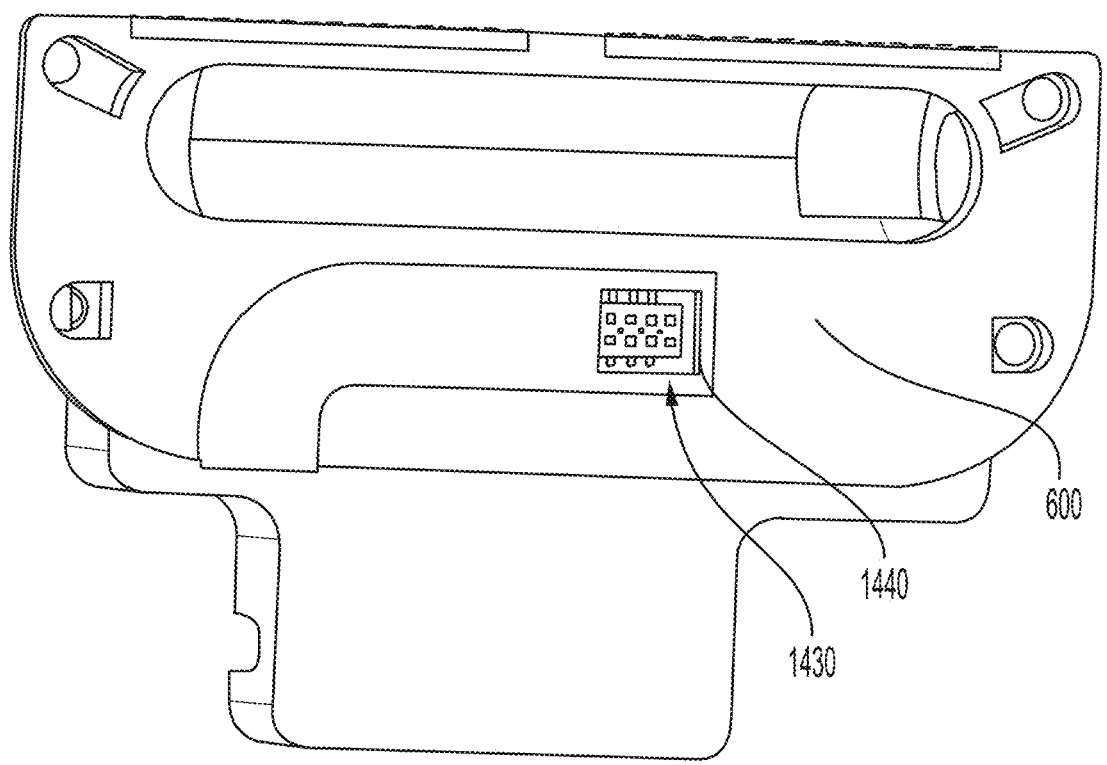
FIG. 15 depicts a lower side of the casing illustrated in FIG. 14.

Another embodiment illustrated in FIGS. 14 and 15 is similar to that of FIGS. 12 and 13, but instead of utilizing press fit pins 1210 make contact to electrical contacts 1220 in the circuit board 530 and provide a conductive path for high voltage electrical therapy to the conductive surface 410 on the second side 305B (lower side) of the substrate or base plate 305, an interconnect board 1410 is used to make the high voltage connection. The interconnect board 1410 includes a board-to-board connector 1420 which mates with a complimentary connector 1430 in the circuit board 530 through an aperture 1440 in a lower side of the casing 600. The board-to-board connector 1420 and/or connector 1430 may include one or more pins that engage one or more receiving connectors in the other of the board-to-board connector 1420 or connector 1430. The interconnect board 1410 includes one or more high voltage traces 1450 which electrically connect the board-to-board connector 1420 to the conductive tab 780 that is electrically connected to the conductive surface 410 on the second side 305B (lower side) of the substrate or base plate 305. In this example, the gas generator can be connected in a similar manner as shown in FIG. 10, e.g., using a 2-position IP rated connector 1010.

Figure 16:
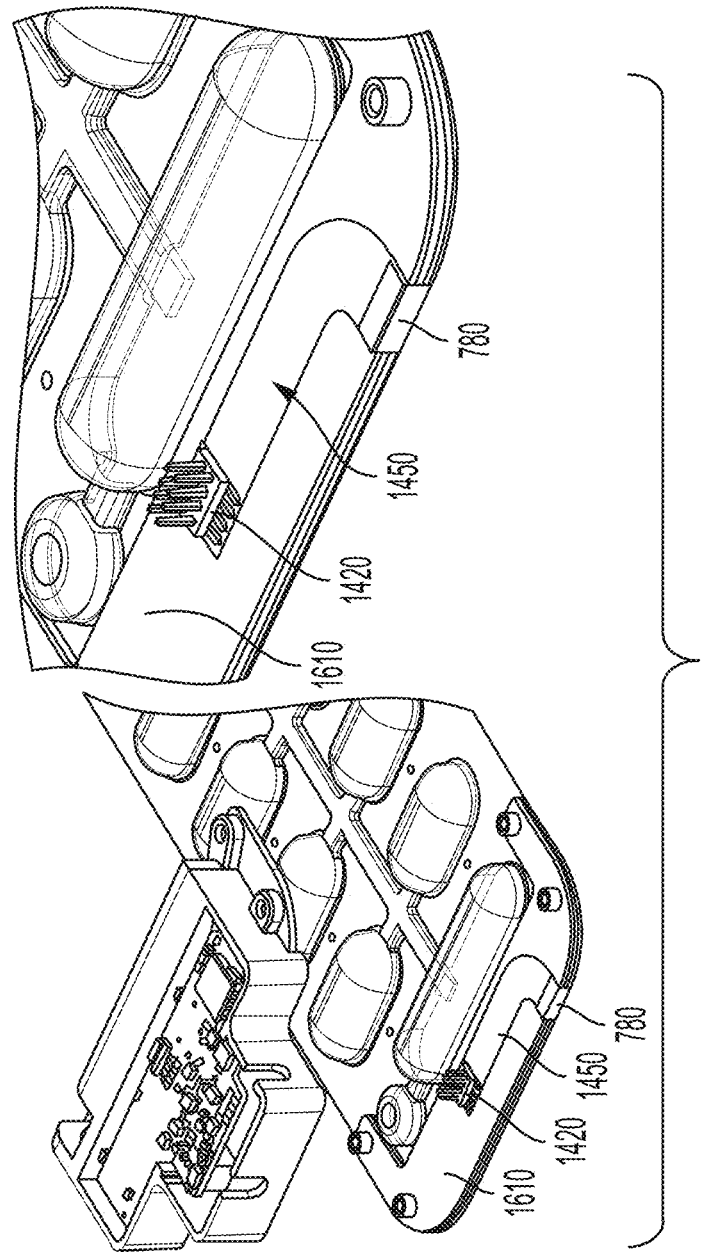
FIG. 16 depicts another example of a therapy electrode assembly including a board-to-board connector for a high voltage connection.

A further embodiment, illustrated in FIG. 16, is similar to that illustrated in FIGS. 14 and 15, however, instead of a rigid interconnect board 1410, a flex circuit 1450 is used. The flex circuit 1450 includes conductive traces running between the board-to-board connector 1420 and the connection to the nickel tab 780. This allows for the board-to-board connector 1420 to be connected before the casing 600 is assembled to the mounting plate (no longer a blind connection). It also allows for a predesigned amount of misalignment between the connectors 1420, 1430 as compared to the embodiment of FIGS. 14 and 15. The embodiment of FIG. 16 further includes a silicone gasket 1610 gasket for keeping debris out of the space between the enclosure and mounting plate. The silicone gasket 1610 may be similar to the mounting plate gasket 1230 illustrated in FIGS. 12-14. In this example, the gas generator can be connected in a similar manner as shown in FIG. 10, e.g., using a 2-position IP rated connector 1010.

In a first example use case, a user wears a wearable therapeutic device including a garment as illustrated in FIG. 1 and multiple therapeutic electrode components 300 as illustrated in FIG. 3 removably disposed within the garment. The user receives a notification, either from the controller of the wearable therapeutic device, from a provider of the wearable therapeutic device, or a medical service person that the conductive fluid in one or more of the therapeutic electrode components 300 has reached its expiration date. The user or medical service person acquires one or more new base plates including receptacles filled with fresh conductive fluid. The user or medical service person removes the casing including the circuit board from the one or more therapeutic electrode components that have expired conductive fluid. The user or medical service person then attaches replacement casings including circuit boards into the one or more new base plates. The old base plates with the expired conductive fluid may be discarded or returned to the provider.

In a second example use case, a user again wears a wearable therapeutic device including a garment as illustrated in FIG. 1 and multiple therapeutic electrode components 300 as illustrated in FIG. 3 removably disposed within the garment. The user receives a notification, for example, from the provider of the wearable therapeutic device or a or medical service person that one or more of the gas charges in one or more of the therapeutic electrode components disposed in the garment have been discovered to belong to a batch that has been experiencing failures, for example, failures to release gas after receiving an activation current. The provider sends the user or medical service person one or more replacement base plates including gas charges from a different batch. The user or medical service person removes the casings including the circuit boards from the one or more therapeutic electrode components that have the suspected bad gas charges, attaches the casings including the circuit boards to the replacement base plates, and reinstalls the therapy electrode components into their respective locations in the garment. The old base plate modules with the suspected bad gas charges may be discarded or returned to the provider.

It should be appreciated that in either of the example use cases described above, the user of the medical device may be capable of performing the replacement of the portions of the therapy electrode component(s). In other examples, these operations may be performed by a provider of the medical device, for example, by the user sending a wearable medical device including one or more of the therapy electrode components to a provider for service or refurbishment.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A modular waterproof therapeutic electrode component for preventing water ingress and for servicing, comprising:
    a substrate comprising a conductive surface,
    a reservoir of conductive fluid mounted on the substrate,
    a reusable waterproof enclosure comprising circuitry, the reusable waterproof enclosure configured to be removably coupled to the substrate;
    a gas cartridge in electrical communication with the circuitry and mounted on the substrate, the gas cartridge configured to cause the reservoir to release the conductive fluid onto the conductive surface to reduce electrical impedance between the conductive surface and skin of a subject; and
    a mounting plate disposed on an upper surface of the substrate, the mounting plate providing a conduction path for high voltage electrical therapy from the circuitry to the conductive surface.

2. The component of claim 1, wherein the mounting plate comprises pins configured to make contact with corresponding electrical contacts on a circuit board, the circuit board comprising the circuitry comprised in the reusable waterproof enclosure.

3. The component of claim 1, wherein the conductive surface is a lower surface of the substrate and the reusable waterproof enclosure is configured to be removably coupled to the mounting plate.

4. A modular waterproof therapeutic electrode component for preventing water ingress and for servicing, comprising:
    a substrate comprising a conductive lower surface;
    a reservoir of conductive fluid mounted on the substrate opposite the conductive lower surface;
    a gas generator also mounted on the substrate, the gas generator configured to supply pressurized gas to the reservoir and cause the reservoir to release the conductive fluid onto the conductive lower surface to reduce electrical impedance between the conductive lower surface and skin of a subject;
    a circuit board encapsulated within a waterproof enclosure, the waterproof enclosure removably coupled to the substrate;
    a waterproof high voltage electrical connector extending from the circuit board and beyond the waterproof enclosure, the waterproof high voltage electrical connector removably electrically connectable to the conductive lower surface of the substrate for delivering electrical stimulus to the subject; and
    a waterproof gas generator connector extending from the circuit board and beyond the waterproof enclosure, the waterproof gas generator connector having a first portion including first electrical conductors extending from the circuit board for delivering an activation signal to the gas generator, and a second portion of the waterproof gas generator connector mechanically engageable with and mechanically disengageable from the first portion, the second portion including second electrical conductors extending to the gas generator for delivering the activation signal to the gas generator.

5. The component of claim 4, wherein the waterproof enclosure, waterproof high voltage electrical connector, and waterproof gas generator connector has a liquid ingress protection rating of at least one of IPX3, IPX4, IPX5, IPX6, IPX7, or IPX8 as specified in international standard EN 60529 (British BS EN 60529: 1992, European IEC 60509: 1989), the waterproof enclosure has a solid particle ingress protection rating of one of IP3X, IP4X, IP5X, or IP6X as specified in international standard EN 60529 (British BS EN 60529:1992, European IEC 60509:1989), and the waterproof gas generator connector has an ingress protection rating of at least one of IP66, IP67, or IP68 as defined in international standard EN 60529 (British BS EN 60529: 1992, European IEC 60509:1989).

6. The component of claim 4, wherein the waterproof enclosure of the circuit board comprises a solid overmolding formed of a waterproof thermoplastic material disposed within a sealed housing.

7. The component of claim 6, further comprising a mounting plate disposed on the substrate and including threaded fittings, the sealed housing including a plurality of apertures providing for fasteners to pass through the sealed housing and engage the threaded fittings of the mounting plate to secure the sealed housing to the substrate, the mounting plate being a conductive plate electrically connected to the conductive lower surface of the substrate, the waterproof high voltage electrical connector including one or more pins extending from the mounting plate and configured to engage respective electrical contacts disposed on the circuit board when the sealed housing is secured to the substrate.

8. The component of claim 7, further comprising an interconnect board captured within the mounting plate and including high voltage conductive traces electrically connected to the conductive lower surface of the substrate, the waterproof high voltage electrical connector including one or more pins extending from the interconnect board and configured to engage respective electrical contacts disposed on the circuit board when the sealed housing is secured to the substrate, the high voltage conductive traces and high voltage electrical connector capable of withstanding voltages of between 1000 volts and 3500 volts and currents of between 1 ampere and 250 amperes.

9. The component of claim 7, further comprising a flexible circuit disposed on the substrate and including a high voltage conductive trace electrically connected to the conductive lower surface of the substrate, the waterproof high voltage electrical connector including one or more pins extending from the flexible circuit and configured to engage respective electrical contacts disposed on the circuit board when the sealed housing is secured to the substrate.

10. The component of claim 4, wherein the waterproof high voltage electrical connector includes a conductive lead electrically connected to a conductive tab disposed on the substrate that is electrically connected to the conductive lower surface of the substrate, the conductive lead being electrically connected to the conductive tab with solder to allow the conductive lead to be disconnected from the conductive tab by melting the solder, the conductive lead terminating in a pin that is connected to the conductive tab via a soldered crimp connection.

11. The component of claim 4, wherein the component is disposed in a garment wearable on a torso of the subject along with electrocardiogram (ECG) electrodes for detecting an ECG of the subject, a monitor and controller for receiving ECG signals from the ECG electrodes and detecting arrhythmias, and a user interface to warn the subject of an impending electrical stimulus to be delivered to the subject via the component, the user interface providing for the subject to respond to the warning to abort delivery of the electrical stimulus.

12. A wearable therapeutic device including modular waterproof components for servicing after use in a wearable medical device for application of electrical stimulus to a subject, comprising:
   a plurality of modular waterproof therapeutic electrode components, at least one of the plurality of modular waterproof therapeutic electrode components including:
      a substrate comprising a conductive lower surface,
      a reservoir of conductive fluid mounted on the substrate opposite the conductive lower surface,
      a gas generator also mounted on the substrate, the gas generator configured to supply pressurized gas to the reservoir and cause the reservoir to release the conductive fluid onto the conductive lower surface to reduce electrical impedance between the conductive lower surface and skin of the subject,
      a circuit board encapsulated within a waterproof enclosure, the waterproof enclosure and removably coupled to the substrate,
      a waterproof high voltage electrical connector extending from the circuit board and beyond the waterproof enclosure, the waterproof high voltage electrical connector removably electrically connectable to the conductive lower surface of the substrate for delivering the electrical stimulus to the subject, and
      a waterproof gas generator connector extending from the circuit board and beyond the waterproof enclosure, the waterproof gas generator connector having a first portion including first electrical conductors extending from the circuit board for delivering an activation signal to the gas generator, and a second portion of the waterproof electrical connector mechanically engageable with and mechanically disengageable from the first portion, the second portion including second electrical conductors extending to the gas generator for delivering the activation signal to the gas generator;
   a waterproof distribution node including waterproof electrical connectors; and
   a wiring harness having waterproof electrical connectors removably connectable to the waterproof electrical connectors of the distribution node for providing electrical communication between the distribution node and each of the plurality of modular waterproof therapeutic electrode components.

13. The device of claim 12, wherein at least one of the plurality of modular waterproof therapeutic electrode components includes an electrical passthrough to deliver electrical signals and an electrical stimulus pulse from the distribution node to another of the plurality of modular waterproof therapeutic electrode components.

14. The device of claim 12, wherein each of the plurality of modular waterproof therapeutic electrode components and waterproof distribution node are disposed in a garment to be worn on a torso of the subject along with electrocardiogram (ECG) electrodes for detecting an ECG of the subject, with a monitor and controller for receiving ECG signals from the ECG electrodes and detecting arrhythmias, and a user interface to warn the subject of an impending electrical stimulus to be delivered to the subject via the plurality of modular waterproof therapeutic electrode components, the user interface providing for the subject to respond to the warning to abort delivery of the electrical stimulus, the waterproof electrical connectors of the waterproof distribution node including an electrical connector configured to provide electrical communication between the ECG electrodes and the waterproof distribution node.

15. The device of claim 14, wherein the waterproof distribution node is encapsulated in a solid overmolding formed of a waterproof thermoplastic material.

16. The device of claim 14, wherein the waterproof electrical connectors of the distribution node includes more than one connector configured to provide communication with more than one respective modular waterproof therapeutic electrode component through the wiring harness, more than one connector configured to provide communication with ECG electrodes, and a connector configured to provide communication with a monitor and controller of the device.

17. The device of claim 12, wherein the waterproof enclosure is configured to be removably coupled to an upper surface of the substrate.

18. The device of claim 12, wherein the waterproof enclosure, the waterproof high voltage electrical connector, and the waterproof gas generator connector each has a liquid ingress protection rating of at least one of IPX3, IPX4, IPX5, IPX6, IPX7, or IPX8 as specified in international standard EN 60529 (British BS EN 60529:1992, European IEC 60509:1989) and the waterproof enclosure has a solid particle ingress protection rating of one of IP3X, IP4X, IP5X, or IP6X as specified in international standard EN 60529 (British BS EN 60529:1992, European IEC 60509:1989).

19. A modular waterproof therapeutic electrode component for preventing water ingress and for servicing, comprising:
   a substrate comprising a conductive surface;
   a reservoir of conductive fluid mounted on the substrate;
   a reusable waterproof enclosure comprising circuitry, the reusable waterproof enclosure configured to be removably coupled to the substrate;
   a gas cartridge in electrical communication with the circuitry and mounted on the substrate, the gas cartridge configured to cause the reservoir to release the conductive fluid onto the conductive surface to reduce electrical impedance between the conductive surface and skin of a subject; and
   an interconnect board disposed on the substrate, the interconnect board including a board-to-board connector that mates with a complimentary connector in the circuitry and that provides a conduction path for high voltage electrical therapy from the circuitry to the conductive surface, wherein the reusable waterproof enclosure is configured to be removably coupled to the interconnect board.

20. A modular waterproof therapeutic electrode component for preventing water ingress and for servicing, comprising:
- a substrate comprising a conductive surface;
- a reservoir of conductive fluid mounted on the substrate;
- a reusable waterproof enclosure comprising circuitry, the reusable waterproof enclosure configured to be removably coupled to the substrate;
- a gas cartridge in electrical communication with the circuitry and mounted on the substrate, the gas cartridge configured to cause the reservoir to release the conductive fluid onto the conductive surface to reduce electrical impedance between the conductive surface and skin of a subject;
- a waterproof high voltage electrical connector extending from the circuitry and beyond the reusable waterproof enclosure, the waterproof high voltage electrical connector removably electrically connectable to the conductive surface of the substrate for delivering electrical stimulus to the subject; and
- a waterproof fluid deployment device connector extending from the circuitry and beyond the reusable waterproof enclosure, the waterproof fluid deployment device connector having a first portion including first electrical conductors extending from the circuitry for delivering an activation signal to the gas cartridge, and a second portion of the waterproof fluid deployment device connector mechanically engageable with and mechanically disengageable from the first portion, the second portion including second electrical conductors extending to the fluid deployment device for delivering the activation signal to the gas cartridge.

21. The component of claim 20, wherein the waterproof enclosure, the waterproof high voltage electrical connector, and the waterproof fluid deployment device connector each has a liquid ingress protection rating of at least one of IPX3, IPX4, IPX5, IPX6, IPX7, or IPX8 as specified in international standard EN 60529 (British BS EN 60529:1992, European IEC 60509:1989) and the reusable waterproof enclosure has a solid particle ingress protection rating of one of IP3X, IP4X, IP5X, or IP6X as specified in international standard EN 60529 (British BS EN 60529:1992, European IEC 60509:1989).

* * * * *